(12) United States Patent
Kambadur et al.

(10) Patent No.: US 8,309,068 B2
(45) Date of Patent: Nov. 13, 2012

(54) ISOLATED POLYPEPTIDES AND METHODS OF IMPROVING MUSCLE STRENGTH

(75) Inventors: Ravi Kambadur, Hamilton (NZ); Mridula Sharma, Hamilton (NZ); Monica Senna Salerno De Moura, Hamilton (NZ); Carole J. Berry, Hamilton (NZ); Victoria Siriett, Fairview Downs (NZ); Robert Syndecombe Bower, Dunedin (NZ); Gina Diane Nicholas, Hamilton (NZ); Craig Desmond McFarlane, Hamilton (NZ)

(73) Assignee: Myostin Therapeutics Pty Ltd., Brighton East, Victoria (AU)

( * ) Notice: Subject to any disclaimer, the term of this patent is extended or adjusted under 35 U.S.C. 154(b) by 399 days.

(21) Appl. No.: 12/376,289

(22) PCT Filed: Aug. 2, 2007

(86) PCT No.: PCT/NZ2007/000203
§ 371 (c)(1), (2), (4) Date: Jun. 1, 2009

(87) PCT Pub. No.: WO2008/016314
PCT Pub. Date: Feb. 7, 2008

(65) Prior Publication Data
US 2009/0324590 A1 Dec. 31, 2009

Related U.S. Application Data

(60) Provisional application No. 60/835,525, filed on Aug. 3, 2006.

(51) Int. Cl.
*A61K 38/18* (2006.01)
*C07K 14/52* (2006.01)
(52) U.S. Cl. ............ 424/85.2; 530/324; 514/1.1
(58) Field of Classification Search .......... None
See application file for complete search history.

(56) References Cited

U.S. PATENT DOCUMENTS

| | | | | |
|---|---|---|---|---|
| 4,179,337 | A | * | 12/1979 | Davis et al. .......... 435/181 |
| 4,847,325 | A | * | 7/1989 | Shadle et al. .......... 525/54.1 |
| 6,207,160 | B1 | | 3/2001 | Victoria et al. |
| 2007/0190056 | A1 | | 8/2007 | Kambadur et al. |

FOREIGN PATENT DOCUMENTS

| | | |
|---|---|---|
| JP | 2002504326 A | 2/2002 |
| JP | 2004504826 A | 2/2004 |
| WO | WO 98/33887 A1 | 8/1998 |
| WO | WO 99/42573 A1 | 8/1999 |
| WO | WO 01/05820 A2 | 1/2001 |
| WO | WO 01/53350 A1 | 7/2001 |
| WO | WO 02/09641 A2 | 2/2002 |
| WO | WO 02/10214 A2 | 2/2002 |
| WO | WO 2004/011650 A2 | 2/2004 |
| WO | WO 2004/024890 A2 | 3/2004 |
| WO | WO 2005/051993 A1 | 6/2005 |
| WO | WO 2005/066204 A2 | 7/2005 |
| WO | WO 2006/083183 A1 | 8/2006 |

OTHER PUBLICATIONS

Castelhano-Barbosa, E.C. et al. 2005 "Temporal and spatial expression of the Myostatin gene during chicken embryo development" *Growth, Development & Aging* 69:3-12.
Jiang, M.-S. et al. 2004 "Characterization and identification of the inhibitory domain of GDF-8 propeptide" *Biochem and Biophys Res Comm* 315:525-531.
Nicholas, G. et al. 2002 "Titin-Cap associates with, and regulates secretion of, Myostatin" *J Cellular Physiol* 193:120-131.
Dooley, H. et al. 2003 "Selection and characterization of naturally occurring single-domain (IgNAR) antibody fragments from immunized sharks by phage display" *Molec Immunol* 40:25-33.
Dunner, S. et al. 2003 "Haplotype diversity of the *myostatin* gene among beef cattle breeds" *Genet Sel, Evol* 35: 103-118.
Gonzalez-Cadavid, N.F. et al. 1998 "Organization of the human myostatin gene and expression in healthy men and HIV-infected men with muscle wasting" *PNAS USA* 95: 14938-14943.
Jeanplong, F. et al. 2001 "Genomic organization and neonatal expression of the bovine myostatin gene" *Mol Cell Biochem* 220:31-37.
Kambadur, R. et al. 1997 "Mutations in *myostatin* (GDF8) in Double-Muscled Belgian Blue and Piedmontese Cattle" *Genome Res.* 7: 910-916.
Lee, S -J et al 2001 "Regulation of myostatin activity and muscle growth" *Proc Natl Acad Sci USA* 98:9306-9311.
Sawada, Y. et al. 1997 "Stretch-induced Hypertrophic Growth of Cardiocytes and Processing of Brain-type Natriuretic Peptide Are Controlled by Proprotein-processing Endoprotease Furin" *J Biol Chem* 272: 20545.20554.
Sharma, M. et al. 1999 "Myostatin, a transforming growth factor-β superfamily member is expressed in heart muscle and is upregulated in cardiomyocytes after infarct" *J Cell Phys* 180: 1-9.

* cited by examiner

*Primary Examiner* — Prema Mertz
(74) *Attorney, Agent, or Firm* — Knobbe Martens Olson & Bear LLP

(57) ABSTRACT

An isolated recombinant polypeptide having myostatin antagonist activity, comprising a C-terminally truncated mature myostatin peptide, wherein the C-terminal truncation is at a position at or between amino acids 281 and 329, or a fragment, variant or derivative thereof.

13 Claims, 18 Drawing Sheets

| | | |
|---|---|---|
| MurineMyostatin | aa268 | DFGLDCDEHSTESRCCRYPLTVDFEAFGWDWIIAPKRYKANYCSGECEFVFLQKYPHT |
| HumanMyostatin | aa267 | DFGLDCDEHSTESRCCRYPLTVDFEAFGWDWIIAPKRYKANYCSGECEFVFLQKYPHT |
| ChickenMyostatin | aa267 | DFGLDCDEHSTESRCCRYPLTVDFEAFGWDWIIAPKRYKANYCSGECEFVFLQKYPHT |
| DogMyostatin | aa268 | DFGLDCDEHSTESRCCRYPLTVDFEAFGWDWIIAPKRYKANYCSGECEFVFLQKYPHT |
| RatMyostatin | aa268 | DFGLDCDEHSTESRCCRYPLTVDFEAFGWDWIIAPKRYKANYCSGECEFVFLQKYPHT |
| BovineMyostatin | aa267 | DFGLDCDEHSTESRCCRYPLTVDFEAFGWDWIIAPKRYKANYCSGECEFVFLQKYPHT |
| OvineMyostatin | aa267 | DFGLDCDEHSTESRCCRYPLTVDFEAFGWDWIIAPKRYKANYCSGECEFLFLQKYPHT |

| | | |
|---|---|---|
| MurineMyostatin | VHQANPRGSAGPCCTPTKMSPINMLYFNGKEQIIYGKIPAMVVDRCGCS | aa376 |
| HumanMyostatin | VHQANPRGSAGPCCTPTKMSPINMLYFNGKEQIIYGKIPAMVVDRCGCS | aa375 |
| ChickenMyostatin | VHQANPRGSAGPCCTPTKMSPINMLYFNGKEQIIYGKIPAMVVDRCGCS | aa375 |
| DogMyostatin | VHQANPRGSAGPCCTPTKMSPINMLYFNGKEQIIYGKIPAMVVDRCGCS | aa375 |
| RatMyostatin | VHQANPRGSAGPCCTPTKMSPINMLYFNGKEQIIYGKIPAMVVDRCGCS | aa376 |
| BovineMyostatin | VHQANPRGSAGPCCTPTKMSPINMLYFNGEGQIIYGKIPAMVVDRCGCS | aa375 |
| OvineMyostatin | VHQANPKGSAGPCCTPTKMSPINMLYFNGKEQIIYGKIPGMVVDRCGCS | aa375 |

Accession Numbers:

| | |
|---|---|
| Murine | NP_034964 |
| Human | NP_005250 |
| Chicken | NP_001001461 |
| Dog | NP_001002959 |
| Rat | NP_062024 |
| Bovine | NP_001001525 |
| Ovine | O18830 |

FIGURE 31

ISOLATED POLYPEPTIDES AND METHODS OF IMPROVING MUSCLE STRENGTH

This application is U.S. National Phase of International Application PCT/NZ2007/000203, filed Aug. 2, 2007 designating the U.S., and published in English as WO 2008/016314 on Feb. 7, 2008, which claims priority to U.S. Provisional Application No. 60/835,525 filed Aug. 3, 2006.

FIELD OF THE INVENTION

The present invention relates to novel proteins with myostatin antagonist activity. The present invention further relates to the use of the novel proteins in the treatment of myostatin related disorders.

BACKGROUND

Myostatin (or GDF-8) is a negative regulator of muscle growth and is structurally related to the transforming growth factor β (TGF-β) superfamily (McPherron et al 1997a). More particularly, myostatin is a potent negative regulator of skeletal muscle during development, and in adult life. Myostatin is also found in a wide range of species from fish to mammals and the myostatin protein is highly conserved and homologous across species (McPherron and Lee, 1997a). Myostatin exerts its biological effects through interaction with the cell surface receptor activin type IIB (Lee et al, 2001). Myostatin is also known to regulate its own expression via a mechanism that is incompletely understood at present (Spiller et al., 2002, Rebbapragada et al, 2003).

It has been demonstrated that myostatin inhibits myoblast proliferation and differentiation without inducing apoptosis or stimulating muscle protein breakdown (Thomas et al, 2000; Langley et al, 2002; Rios et al, 2001; Taylor et al, 2001). Knock-out mice for myostatin have greatly increased muscle mass over their entire body. Myostatin-null mice have approximately 30% greater body weight than normal mice, and exhibit a 2-3 fold increase in individual muscle weight due to muscle fibre hyperplasia and hypertrophy. Natural mutations in myostatin have been identified as being responsible for the "double-muscled" phenotype, such as the Belgian Blue and Piedmontese cattle breeds (McPherron et al, 1997b; Kambadur et al, 1997; Grobet et al, 1997). A similar phenotype has been observed in a human that has a defective myostatin gene (Schuelke et al, 2004). The interpretation of the role of myostatin in various biological processes via studies of myostatin null animals has been confounded by inability to distinguish between pre-natal developmental effects and effects that relate to the lack of myostatin during juvenile and adult life.

However, myostatin has been implicated in a number of disorders associated with muscle wasting, or muscle atrophy, such as that seen in individuals affected by HIV, cancer, prolonged bed rest, muscular dystrophy or in age related sarcopenia (Gonzalez-Cadavid et al, 1998; Langley et al, 2004; Zachwieja et al, 1999; Bogdanovich et al, 2002; WO2006/083183). It was demonstrated that in vivo administration of myostatin induces cachexia, a severe form of muscle wasting associated with cancer and sepsis (Zimmers et al, 2002) and that may also occur as a result of extended bed rest. Furthermore, up-regulation of myostatin in glucocorticoid-induced muscle atrophy has been observed (Ma et al, 2003). Changes in myostatin expression have been shown in other conditions, for example, up-regulated in cardiomyocytes after heart damage, and down regulated in regenerating muscle (Sharma et al, 1999).

Myostatin has also been linked with many other biological processes. For example, knockout transgenic mice have altered cortical bone structure indicating a role in osteogenesis (Hamrick 2003). Furthermore, myostatin has been shown to be involved in regulating glucose and fat metabolism, thus it may be implicated in type 2 diabetes and obesity (McPherron and Lee, 2002). Myostatin has also been shown to be involved in the inflammatory response during wound healing (WO2006/083182).

The key role played by myostatin in the regulation of muscle growth and differentiation and the pathology of many diseases and disorders has led to the search for antagonists of myostatin. Whilst many myostatin antagonists have been developed, such as anti-myostatin antibodies (U.S. Pat. No. 6,096,506 and U.S. Pat. No. 6,468,535); a truncated activin type IIB receptor, myostatin pro-domain and follistatin (WO 02/085306); myostatin inhibitors released into culture from cells overexpressing myostatin (WO 00/43781); dominant negatives of myostatin (WO 01/53350); and small peptides including the WMCPP domain which binds to and inhibits myostatin (US 2004/0181033); there are currently no myostatin antagonists in clinical use. Thus, there still exists a need to develop more potent myostatin antagonists for use as therapeutic agents.

Accordingly, it is an object of the invention to provide proteins with myostatin antagonist activity for the treatment of myostatin related disorders, and/or to provide the public with a useful choice.

SUMMARY OF THE INVENTION

The present invention is directed to novel, recombinantly produced peptides having myostatin antagonist activity.

In one aspect the present invention provides for an isolated recombinant polypeptide having myostatin antagonist activity, comprising a C-terminally truncated mature myostatin peptide, wherein the C-terminal truncation is at a position at or between amino acids 281 and 329, or a fragment, variant or derivative thereof.

The isolated recombinant polypeptide may be selected from the group consisting of a C-terminally truncated mature myostatin peptide wherein the C-terminal truncation is at amino acid position 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328 or 329, or a fragment, variant or derivative thereof.

Preferably the isolated recombinant polypeptide of the invention is selected from the group consisting of a C-terminally truncated mature myostatin polypeptide, wherein the C-terminal truncation is at amino acid position 329, 320, 310, 300, 295, 289, 284, 282 or 281 (SEQ ID NOS: 3-11), or a fragment, variant or derivative thereof, or a polypeptide having substantial sequence homology thereto.

More preferably the isolated recombinant polypeptide of the invention is selected from the group consisting of a C-terminally truncated mature myostatin polypeptide, wherein the C-terminal truncation is at amino acid position 320, 310 or 300 (SEQ ID NOS: 4-6) or a fragment, variant or derivative thereof, or a polypeptide having substantial sequence homology thereto.

The invention also provides for an isolated polynucleotide comprising a nucleotide sequence that encodes a polypeptide of the invention, or a complementary sequence thereto.

Variants of the polypeptide and polynucleotide sequences of the invention may be desirable as a way to produce a myostatin antagonist having selectively altered binding characteristics or having improved biodistribution or half life in vivo or on the shelf.

Preferably the myostatin antagonist polypeptide of the invention is part of a fusion protein including, in addition to the antagonist, one or more polypeptides that enhance one or more functions selected from the group consisting of purification, formation of protein complexes, tissue localization or distribution, uptake/administration, in vivo stability and/or in vivo half life. For example, the fusion protein can include an immunoglobulin Fc domain such as an IgG1 Fc fragment. The fusion protein may include a purification subsequence, such as an epitope tag, a FLAG tag, a polyhistidine sequence, or a GST fusion. Preferably the tag sequences comprise SEQ ID NO: 13 and 14.

The myostatin antagonist polypeptide of the invention may include one or more modified amino acid residues, such as a glycosylated amino acid, a PEGylated amino acid, a farnesylated amino acid, an acetylated amino acid, a biotinylated amino acid, an amino acid conjugated to a lipid moiety, a D amino acid or an amino acid conjugated to an organic derivatizing agent.

The invention also provides for a pharmaceutical composition comprising at least one isolated polypeptide of the invention together with a pharmaceutically acceptable carrier.

The present invention also provides a method of regulating muscle growth, promoting adipogenic differentiation and/or promoting bone growth or mineralization in an animal comprising administering to said animal an effective amount of at least one polypeptide of the invention. Preferably, the method may be used to produce increased muscle mass, decreased fat deposition and/or improved bone growth in a sheep, cattle, deer, poultry, turkey, pig, horse, mouse, rat, cat, dog or human.

The animal may have normal or abnormal levels of myostatin. In animals with normal levels of myostatin, treatment with the antagonists of the invention will result in increased muscle mass. In animals with normal muscle mass, such treatment will result in an increase in muscle mass and may be particularly useful in the meat production industry. In animals with reduced muscle mass, due to muscle damage or trauma, wasting due to bed rest, etc, treatment with the antagonists of the invention will restore the muscle mass to normal. In animals with abnormal myostatin levels, the muscle mass will invariably be reduced and treatment with myostatin antagonists of the invention will restore the muscle mass back towards normal levels.

The invention also provides a method to prevent, treat or reduce the severity of a myostatin related pathologic condition, which is characterized, at least in part, by an abnormal amount, development or metabolic activity of muscle or adipose tissue in a patient, wherein said method comprises administering an effective amount of at least one polypeptide of the invention to a patient in need thereof.

The pathologic condition may include disorders related to muscle hypertrophy; muscle atrophy and muscle wasting associated with inflammatory myopathies, muscular dystrophies, motor neuron diseases, diseases of the neuromuscular junction, diseases of the peripheral nerve, myopathies due to endocrine abnormalities, metabolic syndrome, HIV, cancer, sarcopenia, cachexia, inactivity or prolonged bedrest and other wasting conditions; cardiac failure; osteoporosis; renal failure or disease; liver failure or disease; anorexia; obesity; diabetes; and wound healing.

As another alternative a polypeptide of this invention may be conjugated to another pharmaceutically active compound to enhance the therapeutic effect on the target cell or tissue by delivering a second compound in an effort to treat the diseases or therapeutic indications stated above. In these combinations, the myostatin antagonist of the invention may be independently and sequentially administered or co-administered.

The present invention also provides a method of regulating muscle growth of an animal comprising administering to said animal an effective amount of at least one polypeptide of the invention. Preferably, the method may be used to produce increased muscle mass in a sheep, cattle, deer, poultry, turkey, pig, horse, mouse, rat, cat, dog or human.

BRIEF DESCRIPTION OF THE FIGURES

The invention will be further described with reference to the following figures in which:

FIG. 29 shows the myoblast proliferation assay results of the mimetics 280 and 329 at three concentrations (1, 5 and 10 µg/ml) in addition to 300 10 µg/ml at positive control after 48 hours and 72 hours; and.

FIGS. 30 C and D show H&E staining of the muscle. Saline treated muscle (C) shows necrotic, degenerating fibres. 300 antagonist treated muscle (D) shows darker stained fibres, many with centrally formed nuclei, indicating nascent and regenerating fibres.

FIG. 31 shows the high sequence homology of the myostatin sequence across species.

EXEMPLARY DEFINITIONS

Figure 1:
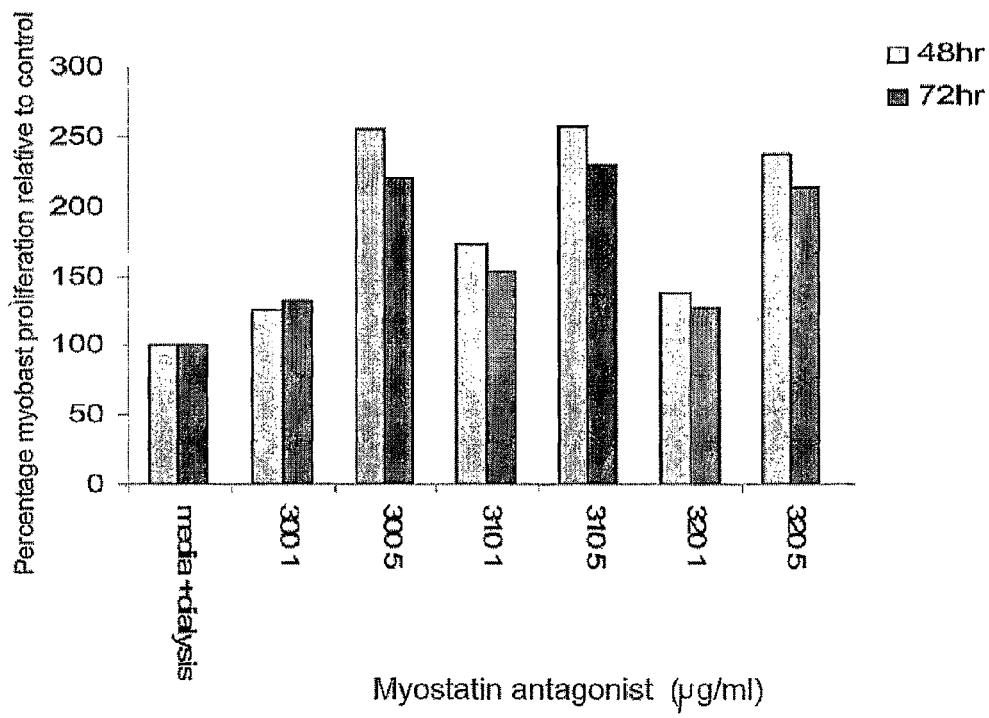
FIG. 1 shows the effect of myostatin antagonists 300, 310 and 320 (at 1 and 5 µg/ml) on C2C12 myoblast proliferation. The myoblasts were cultured for 48 and/or 72 hours.

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

"Hypertrophy" as used throughout the specification and claims means any increase in cell size.

"Hyperplasia" as used throughout the specification and claims mean any increase in cell number.

"Muscle atrophy" as used throughout the specification and claims means any wasting or loss of muscle tissue resulting from the lack of use.

"Sarcopenia" as used throughout the specification and claims means a decline in muscle mass and performance caused by old age, as well as sarcopenia-related or other age-related muscle disorders characterised by muscle atrophy and a decrease in the ability of satellite cells to become activated.

"Inhibitor" or "antagonist" of myostatin as used throughout the specification and claims means any compound that acts to decrease, either in whole or in part, the activity of myostatin.

"Muscle growth" is to be understood as meaning the division and/or differentiation of muscle cells and includes the division and/or differentiation of any precursor cell, fusion of such cells with each other and/or with existing muscle fibres, and it also includes increased protein synthesis in myofibres leading to higher protein content and greater muscle fibre volume (muscle fibre hypertrophy).

The term "polynucleotide" is to be understood as meaning a polymer of deoxyribonucleic acids or ribonucleic acids, and includes both single stranded and double stranded polymers, including DNA, RNA, cDNA, genomic DNA, recombinant DNA, nucleic acid molecules prepared from natural or artificial nucleosides or nucleotides, and all other known forms of polynucleotides. The polynucleotide may be isolated from a naturally occurring source, produced using recombinant or molecular biological techniques, or produced synthetically. A polynucleotide may include a whole gene or any part thereof, and does not have to include an open reading frame. The use of all polynucleotides according to the present invention includes any and all open reading frames. Open reading frames can be established using known techniques in the art. These techniques include the analysis of polynucleotide sequences to identify known start and stop codons. Many computer software programmes that can perform this function are known in the art.

A "protein", "peptide" or "polypeptide" is to be understood as meaning a polymer of naturally occurring and/or artificial amino acids covalently linked via peptide bonds. A polypeptide includes a polypeptide that has been isolated from a naturally occurring source, or produced using recombinant techniques. It is to be appreciated that a polypeptide that includes a leader or pro-sequence, or a polypeptide that undergoes a post translational modification is intended to fall within the definition of a polypeptide. This term does not include a polypeptide that has been synthetically produced, as synthetic polypeptides can be problematic. In particular, synthetically made polypeptides may not fold correctly, and thus may not have the biological activity associated with a naturally occurring or recombinantly produced polypeptide.

The term "fragment or variant" is to be understood to mean any polynucleotide or polypeptide sequence or partial sequence that has been modified by substitution, insertion or deletion of one or more nucleotides or one or more amino acids, but that has substantially the same activity or function as the unmodified sequence or partial sequence.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine, and valine; glycine, and alanine; asparagine and glutamine; and serine, threonine, phenylalanine, and tyrosine. Other groups of amino acids that may represent conservative changes include (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Amino acids may be classified according to the nature of their side groups. Amino acids with nonpolar alkyl side groups include glycine, alanine, valine, leucine, and isoleucine. Serine and threonine have hydroxyl groups on their side chains, and because hydroxyl groups are polar and capable of hydrogen bonding, these amino acids are hydrophilic. Sulfur groups may be found in methionine and cysteine. Carboxylic acid groups are part of the side chain of aspartic acid and glutamic acid, which because of the acidity of the carboxylic acid group, the amino acids are not only polar but can become negatively charged in solution. Glutamine and asparagine are similar to glutamic acid and aspartic acid except the side chains contain amide groups. Lysine, arginine, and histidine have one or more amino groups in their side chains, which can accept protons, and thus these amino acids act as bases. Aromatic groups may be found on the side chains of phenylalanine, tyrosine, and tryptophan. Tyrosine is polar because of its hydroxyl group, but tryptophan and phenylalanine are nonpolar. A variant may also, or alternatively, contain nonconservative changes.

A polypeptide variant according to the invention may have at least one substitution, addition, insertion, or deletion and may be made according to mutagenesis methods known in the art. Such modifications may be made to a polynucleotide sequence that encodes a polypeptide variant or derivative of the invention and may be introduced using standard mutagenesis techniques, such as oligonucleotide-directed site-specific mutagenesis. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Oligonucleotide-directed site-specific mutagenesis procedures can also be employed to provide an altered encoding polynucleotide wherein predetermined codons can be altered by substitution, deletion, or insertion by methods well known in the art.

Alternatively, a variety of computational methods can be used to generate variant myostatin antagonist proteins of the invention, including sequence based methods and structure based methods such as protein design automation (PDA) as described in U.S. Pat. No. 6,403,312.

It should also be appreciated that software is available to very accurately predict the three dimensional structure of a peptide sequence (Bradely, 2005). Therefore, it will be possible for someone skilled in the art to use such software to predict the effect of variations to the peptide sequence on structure of the peptide and therefore any likely effect on the activity of the peptide. Such variations are also incorporated within the scope of the present invention.

A "derivative" polypeptide of the invention means that the amino acid sequence has been altered in some way to produce a polypeptide having greatly increased stability. For example, amino acids can be replaced by the same amino acid of different chirality, or non-naturally occurring amino acids can be inserted or substituted in the polypeptide. Alternatively, the polypeptide may be chemically modified to improve pharmacokinetics, such as by crosslinking with polymers such as polyethylene glycol (U.S. Pat. No. 4,640,835). Such derivatives may have increased serum half lives in vivo, bioavailability, dissociation rates and other properties that make them very useful in formulating pharmaceutical compositions.

A polypeptide of the invention, or a fragment, variant or derivative thereof has the biological function of antagonising myostatin activity. To determine whether a polypeptide of the invention, or a fragment, variant or derivative thereof, is able to antagonise myostatin activity, such activity can be tested by growing myoblasts in the presence or absence (control) of a candidate polypeptide of the invention. An increase in the growth of myoblasts, which produce myostatin and therefore limit their own rate of proliferation, over control myoblasts that did not receive the candidate polypeptide indicates that the peptide has myostatin antagonistic activity. A suitable cell line could be murine $C_2C_{12}$ myoblasts (ATCC NO: CRL-1772), however, it will be appreciated that any suitable myoblast cell line could be used, such as primary ovine, bovine, porcine or human myoblasts.

The term "isolated" as used herein refers to removal of a molecule such as a polypeptide or encoding polynucleotide from its natural source, environment or milieu (e.g., removal of a protein from an intact cell source), and the term "purified" as used herein means that the protein or polypeptide of the invention, or its encoding polynucleotide is essentially free of association with other polynucleotides, proteins or polypeptides, for example, as a purification product of recombinant host cell culture, or as a purified product from a non-recombinant source. An "isolated" polypeptide therefore is one that is removed from its original environment. Preferably, such polypeptides are at least about 70%, 75%, 80%, 85% or 90% pure, at least about 95% pure, or at least about 99% pure, for example, where such a degree of purity refers to the percentage of detectable myostatin antagonist polypeptide or its encoding polynucleotide that is present in a preparation relative to other detectable polynucleotides and/or polypeptides. The term "substantially purified" or "substantially isolated" as used herein means a mixture that contains a molecule such as a myostatin antagonist polypeptide or its encoding polynucleotide that is essentially free of association with other polynucleotides, proteins or polypeptides, but for the presence of known proteins that can be removed using conventional methods, such as by affinity chromatography with a specific antibody or ligand, and which substantially purified or substantially isolated myostatin antagonist polypeptide or encoding polynucleotide retains its biochemical characteristics as described herein or retains at least one of its detectable functional biological activities.

"Gene expression" is to be understood as meaning the initiation of transcription, the transcription of a section of DNA into mRNA, and the translation of the mRNA into a polypeptide. "A modulator of gene expression" is defined as any compound that is able to cause, in a statistically significant fashion, an increase or decrease in gene expression, and may act at any point in the gene expression pathway.

The term 'comprising' as used in this specification and claims means 'consisting at least in part of', that is to say when interpreting independent claims including that term, the features prefaced by that term in each claim all need to be present but other features can also be present.

The terms "substantially corresponds to," "substantially homologous," or "substantial identity" as used herein denotes a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared. The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides. Desirably, which highly homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as, e.g., the FASTA program analysis described by Pearson and Lipian (1988).

As used herein, "% identity" refers to the percentage of identical amino acids situated at corresponding amino acid residue positions in a sequence when two or more polypeptide are aligned and their sequences analyzed using a gapped BLAST algorithm (e.g., Altschul et al., *Nucleic Acids Res.* 25:3389 (1997)), which weights sequence gaps and sequence mismatches according to the default weightings provided by the National Institutes of Health/NCBI database (Bethesda, Md.; see Internet:>www.ncbi.nlm.nih.gov/cgi-bin/BLAST/nph-newblast).

The term "substantially complementary," when used to define either amino acid or nucleic acid sequences, means that a particular subject sequence, for example, an oligonucleotide sequence, is substantially complementary to all or a portion of the selected sequence, and thus will specifically bind to a portion of an mRNA encoding the selected sequence. As such, typically the sequences will be highly complementary to the mRNA "target" sequence, and will have no more than about 1, 2, 3, 4, 5, 6, 7, 8, 9, or 10 base mismatches throughout the complementary portion of the sequence. In many instances, it may be desirable for the sequences to be exact matches, i.e., be completely complementary to the sequence to which the oligonucleotide specifically binds, and therefore have zero mismatches along the complementary stretch. As such, highly complementary sequences will typically bind quite specifically to the target sequence region of the mRNA and will therefore be highly efficient in reducing, and/or even inhibiting the translation of the target mRNA sequence into polypeptide product.

Substantially complementary oligonucleotide sequences will be greater than about 80 percent complementary (or "% exact-match") to the corresponding mRNA target sequence to which the oligonucleotide specifically binds, and will, more preferably be greater than about 85 percent complementary to the corresponding mRNA target sequence to which the oligonucleotide specifically binds. In certain aspects, as described above, it will be desirable to have even more substantially complementary oligonucleotide sequences for use in the practice of the invention, and in such instances, the oligonucleotide sequences will be greater than about 90 percent complementary to the corresponding mRNA target sequence to which the oligonucleotide specifically binds, and may in certain embodiments be greater than about 95 percent complementary to the corresponding mRNA target sequence to which the oligonucleotide specifically binds, and even up to and including 96%, 97%, 98%, 99%, and even 100% exact match complementary to all or a portion of the target mRNA to which the designed oligonucleotide specifically binds.

Percent similarity or percent complementary of any of the disclosed sequences may be determined, for example, by comparing sequence information using the GAP computer program, version 6.0, available from the University of Wisconsin Genetics Computer Group (UWGCG). The GAP program utilizes the alignment method of Needleman and Wunsch (1970). Briefly, the GAP program defines similarity as the number of aligned symbols (i.e., nucleotides or amino acids) that are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess (1986), (2) a penalty of 3.0 for each gap and an additional 0.10 penalty for each symbol in each gap; and (3) no penalty for end gaps.

DETAILED DESCRIPTION OF THE INVENTION

The present invention is directed to novel proteins possessing myostatin antagonist activity for use in the treatment of myostatin related disorders.

Specifically, the present invention is directed to novel dominant negatives of myostatin comprising mature myostatin recombinant peptides having a C-terminal truncation at a position either at or between amino acid positions 281 to 329 of SEQ ID NO: 2, or a fragment, variant or derivative thereof.

The myostatin protein is initially translated as a 375 amino acid precursor molecule having a secretory signal sequence at the N-terminus, a proteolytic processing signal (RSRR) of the furin endoprotease, and nine conserved cysteine residues in the C-terminal region to facilitate the formation of a "cysteine knot" structure. Myostatin is activated by furin endoprotease cleavage at Arg 266 releasing the N-terminal, or "latency-associated peptide" (LAP) and the mature, C-terminal domain, which dimerises to form the active myostatin molecule. After processing, a homodimer of the LAP peptide remains non-covalently bound to the homodimer of mature myostatin in an inactive complex (Lee et al, 2001). Other proteins, for example, follistatin, titin cap, GDFP1, follistatin related gene and hSGT are also known to bind to and regulate the secretion and activation of the latent myostatin complex (Lee and McPherron, 2001; Nicolas et al, 2002; Hill et al, 2002; Hill et al, 2003; Wang et al, 2003). The amino acid sequence of the human myostatin precursor protein molecule is shown in SEQ ID NO:2. The corresponding nucleotide sequence encoding the myostatin precursor protein is shown in SEQ ID NO:1.

Previous myostatin antagonists comprising mature myostatin peptides which are C-terminally truncated at amino acid position 330 or 350 are known (WO 2001/53350). These antagonists are truncated at a position so that key cysteines are retained that are likely to play an important role in determining their three dimensional structure and associated interactions with other molecules. Loss of these key cysteine residues would be expected to negatively impact on their ability to function. For example, a C313Y substitution in the myostatin gene of cattle causes a loss of function resulting in the Piedmontese phenotype (Berry et al, 2002).

Surprisingly, it has been shown for the first time that mature myostatin peptides C-terminally truncated at positions close to or excluding cysteine residues are biologically active. These novel peptides have myostatin antagonist activity and are useful in the treatment of myostatin related disorders. It has been determined that a myostatin peptide that was C-terminally truncated at position 280 that critically removed all but one cysteine from the mysostatin peptide, was not biologically active. The inventors have shown for the first time that at least two cysteine moieties are required in a C-truncated mature myostatin peptide in order to retain biological activity. Without being bound by theory, it is considered that a peptide that has only a single cysteine moiety will not be able to form an appropriate three dimensional structure required for biological activity. It is thought that the recombinantly produced C-terminally truncated myostatin molecules of the invention fold into a number of different active and inactive conformational forms. The exact conformational form of the biologically active peptides is not known. Attempts by the inventors to make synthetic versions of the recombinant peptide of the invention produced only inactive forms (results not shown). It is considered that, for biological activity, recombinantly produced peptides are necessary.

Thus, the present invention provides for an isolated recombinant polypeptide having myostatin antagonist activity, comprising a C-terminally truncated mature myostatin peptide, wherein the C-terminal truncation is at a position at or between amino acids 281 and 329 of SEQ ID NO: 2, or a fragment, variant or derivative thereof.

The isolated recombinant polypeptides of the invention may be selected from the group consisting of a C-terminally truncated mature myostatin peptide wherein the C-terminal truncation is at amino acid position 281, 282, 283, 284, 285, 286. 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328 or 329 of SEQ ID NO: 2 or a fragment, variant or derivative thereof.

Preferably the isolated recombinant polypeptide of the invention is selected from the group consisting of a C-terminally truncated mature myostatin polypeptide, wherein the C-terminal truncation is at amino acid position 329, 320, 310, 300, 295, 289, 284, 282 or 281 (SEQ ID NOS: 3-11), or a fragment, variant or derivative thereof, or a polypeptide having substantial sequence homology thereto.

More preferably the isolated recombinant polypeptide of the invention is selected from the group consisting of a C-terminally truncated mature myostatin polypeptide, where in the C-terminal truncation is at amino acid position 320, 310 or 300 (SEQ ID NOs: 4, 5 or 6)

The polypeptides of this invention can be altered in many ways to produce variants or derivatives having improved pharmacokinetics, as would be appreciated by a skilled worker. For example, functional groups may be added that alter polarity and/or the ability to form hydrogen bonds and will alter the solubility of the polypeptides. Similarly a functional group may alter the stability by changing the serum half-life (Werle et al, 2006) or by controlling the release of the polypeptide from a micelle at the target site. Further a functional group may 10 alter biocompatibility, for example by minimizing the side effects of the polypeptide to the patient. Addition of a functional group capable of binding to target cells or tissues or facilitating the transport into the target cells will enhance delivery and targeting of the polypeptide. It is also understood that the peptides may be truncated from the N-terminal to improve pharmacokinetics.

A functional group conjugated to a polypeptide of this invention may be a biological targeting molecule that binds to a specific biological substance or site. The biological substance or site is the intended target of the delivery and targeting molecule that binds to it, enabling the delivery of the compound to the tissue or cells of interest.

A ligand may function as a biological targeting molecule by selectively binding or having a specific affinity for another substance. A ligand is recognized and bound by a specific binding body or binding partner, or receptor. Examples of ligands suitable for targeting are antigens, haptens, biotin, biotin derivatives, lectins, galactosamine and fucosylamine moieties, receptors, substrates, coenzymes and cofactors among others. Other substances that can function as ligands for delivery and targeting are certain steroids, prostaglandins, carbohydrates, lipids, certain proteins or protein fragments (i.e. hormones, toxins), and synthetic or natural polypeptides with cell affinity. Ligands also include various substances with selective affinity for ligators that are produced through recombinant DNA, genetic and molecular engineering.

Another type of targeting molecule is an antibody, which term is used herein to include all classes of antibodies, monoclonal antibodies, chimeric antibodies, Fab fractions, fragments and derivatives thereof. Other targeting molecules include enzymes, especially cell surface enzymes such as neuraminidases, plasma proteins, avidins, streptavidins, chalones, cavitands, thyroglobulin, intrinsic factor, globulins, chelators, surfactants, organometallic substances, staphylococcal protein A, protein G, cytochromes, lectins, certain resins, and organic polymers. Targeting molecules may include peptides, including proteins, protein fragments or polypeptides which may be produced synthetically or through recombinant techniques known in the art. Examples of peptides include membrane transfer proteins which could facilitate the transfer of the compound to a target cell interior or for nuclear translocation (see: WO 01/15511).

Other modifications to the polypeptides of the invention include conjugates to a biologically compatible polymer such as polyethylene glycol (PEG) and related polymer derivatives. Drug-PEG conjugates have been described as improving the circulation time (prolong serum half-life) before hydrolytic breakdown of the conjugate and subsequent release of the bound molecule thus increasing the drugs efficacy. For example, U.S. Pat. No. 6,214,966 describes the use of PEG and related polymer derivatives to conjugate to drugs such as proteins, enzymes and small molecules to improve the solubility and to facilitate controlled release of the drug. Alternatively, EP 1082105 (WO 99/59548) describes the use of biodegradable polyester polymers as a drug delivery system to facilitate controlled release of the conjugated drug.

The novel polypeptides of the present invention may also be modified in a way to form chimeric molecules comprising the novel polypeptide fused to another, heterologous polypeptide or amino acid sequence. In one embodiment, such a chimeric molecule comprises a fusion of a polypeptide of the invention with a tag polypeptide which provides an epitope to which an anti-tag antibody can selectively bind. The epitope tag is generally placed at the amino-or carboxyl-terminus of the novel polypeptide. Also, provision of the epitope tag enables the tagged polypeptide to be readily purified by affinity purification using an anti-tag antibody or another type of affinity matrix that binds to the epitope tag. In an alternative embodiment, the chimeric molecule may comprise a fusion of a novel polypeptide of the invention with an immunoglobulhi or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., 1988); the c-myc tag and the 8F9, 3C7, 6E10, G4, B7 and 9E10 antibodies thereto (Evan et al., 1985); and the Herpes Simplex virus glycoprotein D (gD) tag and its antibody (Paborsky et al., 1990). Other tag polypeptides include the Flag-peptide (Hopp et al., 1988); the KT3 epitope peptide (Martin et al., 1992); tubulin epitope peptide (Skinner et al., 1991); and the T7 gene 10 protein peptide tag (Lutz-Freyermuth et al., 1990).

As another alternative a polypeptide of this invention may be conjugated to another pharmaceutically active compound to enhance the therapeutic effect on the target cell or tissue by delivering a second compound with a similar myostatin antagonistic effect or a different activity altogether. For example, U.S. Pat. No. 6,051,576 describes the use of co-drug formulations by conjugating two or more agents via a labile linkage to improve the pharmaceutical and pharmacological properties of pharmacologically active compounds. For example, a second myostatin antagonist may be selected from any one or more known myostatin inhibitors. For example, U.S. Pat. No. 6,096,506 and U.S. Pat. No. 6,468,535 disclose anti-myostatin antibodies. U.S. Pat. No. 6,369,201 and WO 01/05820 teach myostatin peptide immunogens, myostatin multimers and myostatin immunoconjugates capable of eliciting an immune response and blocking myostatin activity. Protein inhibitors of myostatin are disclosed in WO 02/085306, which include the truncated Activin type II receptor, the myostatin pro-domain, and follistatin. Other myostatin inhibitors derived from the myostatin peptide are known, and include for example myostatin inhibitors that are released into culture from cells overexpressing myostatin (WO 00/43781); dominant negatives of myostatin (WO 01/53350), which include the Piedmontese allele (cysteine at position 313 is replaced with a tyrosine) and mature myostatin peptides having a C-terminal truncation at a position either at or between amino acid positions 330 to 375. US2004/0181033 also teaches small peptides comprising the amino acid sequence WMCPP, and which are capable of binding to and inhibiting myostatin.

A second pharmacologically active compound having different activity to the myostatin antagonist polypeptide of the invention may be used conjointly with the polypeptide of the invention to treat the myostatin related disorders. For example, the polypeptide may be administered in conjunction with polypeptide growth factors, NSAIDs or COX-2 inhibitors, alpha and beta blockers, ACE inhibitors, bisphosphonates, oestrogen receptor modulators, antihypertensive agents, glutamate antagonists, insulin, antibiotics, protein kinase C inhibitors or various over the counter substances as would be appreciated by a skilled worker.

Other modifications to improve stability and half life include the identification of susceptible amino acid protease cleavage sites within the polypeptides of the invention, and replacement of such amino acids with alternative amino acids to prevent protease degradation of the polypeptide in plasma, in vivo. A person skilled in the art will appreciate what type of functional groups might be added to achieve the desired result in administering the polypeptide to the patient and thereby improving the overall therapeutic index.

The present invention is further directed to analogs, derivation and variants of the polypeptides of the invention having myostatin mimetics activity.

Analogs, derivatives or variants of the peptides of the invention may include sequence modifications or non-sequence modifications. Non-sequence modifications can include acetylation, methylation, phosphomethylation, carboxilation or glycosylation as described above.

The specific recombinantly produced C-terminally-truncated polypeptides exemplified in the present invention are shown in relation to their position on the C-terminal portion of myostatin of SEQ ID NO: 2.

Preferred analogs include peptides whose sequence differs from those of the invention by one or more conservative amino acid substitutions, deletions or insertions which do not affect the biological activity of the peptide. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Examples of conservative substitutions can be taken from Table 1 below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, .beta.-Ala, Acp |
| Histidine | H | Asp, D-Asp, Lys, D-Lys, Tyr |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs include peptides with modifications which influence peptide stability. Such analogs may contain, for example, one or more non-peptide bonds (which replace the peptide bonds) in the peptide sequence. Also included are analogs that include residues other than naturally occurring L-amino acids, e.g. D-amino acids or non-naturally occurring synthetic amino acids, e.g. beta or gamma amino acids and cyclic analogs.

The present invention further contemplates N-terminal truncations of the polypeptides of the invention. Such variants will comprise the C-terminally truncated polypeptides of the present invention whereby the amino acids from the N-terminal end are sequentially removed and whereby such an N-terminally truncated peptide retains myostatin antagonistic activity.

The present invention also contemplates nucleic acid sequences encoding the novel polypeptides of the present invention.

Recent studies suggest that myostatin is a potent regulator of cell cycle progression and functions in part by regulating both the proliferation and differentiation steps of myogenesis (Langley et al., 2002; Thomas et al., 2000). Several studies have demonstrated a role for myostatin not only during embryonic myogenesis, but also in postnatal muscle growth. Studies by Wehling et al (Wehling et al., 2000) and Carlson et al (Carlson et al., 1999) indicated that atrophy-related muscle loss due to hind limb suspension in mice was associated with increased myostatin levels in *M. plantaris*. Increased myostatin levels were also associated with severe muscle wasting seen in HIV patients (Gonzalez-Cadavid et al., 1998). One explanation for the elevated levels of myostatin observed during muscle disuse is that myostatin may function as an inhibitor of satellite cell activation. Indeed this is supported by recent studies which show that a lack of myostatin results in an increased pool of activated satellite cells in vivo and enhanced self-renewal of satellite cells (McCroskery et al., 2003). Myostatin inhibitors have also been shown to increase the activation of satellite cells, as well 20 as to increase the migration of macrophages and myoblasts during muscle regeneration (WO2006/083182) and in wound healing (WO2006/083183).

Methods suitable for assaying for myostatin antagonist activity of the polypeptides of the present invention may be based on any of a variety of known methodologies including known in vivo animal models or in vitro models. For example, potential myostatin antagonists of the invention may first be tested using an in vitro single fibre satellite cell activation assays, myoblasts proliferation assays, bioassay (WO 2003/00120) or myoblast and/or macrophage migration assays, as described below. Myostatin antagonist polypeptides of the invention that are able to increase satellite cell activation, myoblast proliferation and/or myoblast or macrophage migration in vitro, may then be tested for their ability to treat myostatin related disorders in animal models in vivo. Such models include an aged mouse model of sarcopenia (Kirk, 2000); a mouse model of muscular dystrophy (Mdx) (Tanabe et al, 1986); a mouse model of diabetes (Like et al, 1976); a mouse model of obesity (Giridharan et al, 1998); a notexin model of muscle injury (Kirk, 2000); a model of superficial or deep skin wounds (Gillitze et al, 2001); a model of burns (Yang et al, 2005); a mouse cachexia model where dexamethasone is injected into mice to induce muscle wasting (Ma et al, 2003) or a mouse cancer model in which colon adenocarcinoma (C26) cells or Lewis Lung carcinoma (LLC) cells are injected into mice to induce muscle wasting associated with cancer.

The isolated polypeptides of the invention preferably bind to their target with a Kd of 1 μM or less, and more preferably with a Kd of 100 nM, 10 nM or even 1 nM or less.

The present invention is also directed to a pharmaceutical composition comprising at least one novel polypeptide of the invention having myostatin antagonistic activity together with a pharmaceutical or physiologically acceptable carrier.

A polypeptide of this invention or salt thereof may be included in a pharmaceutically acceptable carrier or diluent, ideally in an amount sufficient to deliver to a patient a therapeutically effective amount without causing serious toxic effects in the patient treated. The concentration of active polypeptide in the composition will depend on absorption, distribution, inactivation, and excretion rates of the polypeptide as well as other factors known to those of skill in the art. It is to be noted that dosage values will also vary with the severity of the condition to be alleviated. It is to be further understood that for any particular subject, specific dosage regimens should be adjusted over time according to the individual need and the professional judgement of the person administering or supervising the administration of the compositions. Examples of the techniques and protocols mentioned above can be found in Remington's Pharmaceutical Sciences, $16^{th}$ edition, Oslo, A. (ed), 1980.

Solutions or suspensions used for parenteral, intradermal, subcutaneous, or topical application may include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of toxicity such as sodium chloride or dextrose.

Suitable pharmaceutically acceptable carriers for parenteral application, such as intravenous, subcutaneous, or intramuscular injection, include sterile water, physiological saline, bacteriostatic saline (saline containing 0.9 mg/ml benzyl alcohol) and phosphate-buffered saline. If administered intravenously, preferred carriers are physiological saline or phosphate buffered saline.

Methods for preparing transdermal formulations including topical formulations or transdermal delivery devices such as patches are known to those skilled in the art. For example, see Brown L., and Langer R., *Transdermal Delivery of Drugs* (1988), Annual Review of Medicine, 39:221-229.

Polypeptides of this invention may be prepared with carriers that will protect the polypeptide against rapid elimination from the body, such as through controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid.

Liposomal suspensions are also suitable carriers for the polypeptides of this invention. The polypeptides may be conjugated to a lipid by known methods for incorporation into a liposomal envelope or the compounds may be encapsulated into the liposome. Liposonies may be prepared according to methods known to those skilled in the art, such as is described in U.S. Pat. No. 4,522,811. For example, liposome formulations may be prepared by dissolving appropriate lipid(s) (such as stearoyl phosphatidyl ethanolamine stearoyl phosphatidyl choline, arachadoyl phosphatidy choline, and cholesterol) in an inorganic solvent that is then evaporated, leaving behind a thin film of dried lipid on the surface of the container. An aqueous solution of the active polypeptide of the invention or its monophosphate, and/or triphosphate derivatives are then introduced into the container. The container is then swirled by hand to free the lipid aggregates, thereby forming the liposomal suspension.

For nasal or pulmonary administration, the active ingredients will be in the form of a fine powder or a solution or suspension suitable for inhalation. Alternatively, the active ingredients may be in a form suitable for direct application to the nasal mucosa such as an ointment or cream, nasal spray, nasal drops or an aerosol.

Oral compositions may include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition. Methods for encapsulating compositions (such as in a coating of hard gelatin) for oral administration are well known in the art (Baker, Richard, *Controlled Release of Biological Active Agents*, John Wiley and Sons, 1986). Techniques to overcome various barriers including the mucus-layer barrier, the enzymatic barrier, and the membrane barrier are well known in the art, (Bernkop-Schnurch et al, 2001).

Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a glidant such as colloidal silicon dioxide; a sweetening agent such as sucrose or saccharin; or a flavouring agent such as peppermint, methyl salicylate, or orange flavouring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents. Alternatively, polypeptides of this invention could be administered as a component of an elixir, suspension, syrup, wafer, chewing gum or the like. A syrup may contain, in addition to the active compounds, sucrose as a sweetening agent and certain preservatives, dyes and colourings and flavours.

The present invention is directed to a method of treating a myostatin related pathological condition in a mammal, wherein the method generally comprises at least the step of administering to a mammal in need thereof, an effective amount of at least one polypeptide of the invention having myostatin antagonistic activity, for a time sufficient to prevent, treat or ameliorate the symptoms of said myostatin related pathological condition. In preferred embodiments the mammal is a human that has, is suspected of having, or has been diagnosed with one or more myostatin related pathological conditions.

The pathologic condition is characterized, at least in part, by an abnormal amount, development or metabolic activity of muscle or adipose tissue in a mammal and may include disorders related to muscle hypertrophy; muscle atrophy and muscle wasting associated with inflammatory myopathies, muscular dystrophies, motor neuron diseases, diseases of the neuromuscular junction, diseases of the peripheral nerve, myopathies due to endocrine abnormalities, metabolic syndrome, HIV, cancer, sarcopenia, cachexia and other wasting conditions; cardiac failure; osteoporosis; renal failure or disease; liver failure or disease; anorexia; obesity; diabetes; and wound healing.

Inflammatory myopathies that can be treated include: Dermatomyositis (PM/DM), Inclusion Body Myositis (IBM) and Polymyositis (PM/DM).

Muscular dystrophies that can be treated include: Becker Muscular Dystrophy (BMD), Congenital Muscular Dystrophy (CMD), Distal Muscular Dystrophy (DD), Duchenne Muscular Dystrophy (DMD), Emery-Dreifuss Muscular Dystrophy (EDMD), Limb-Girdle Muscular Facioscapulohumeral Muscular Dystrophy (FSH or FSHD), Dystrophy (LGMD), Myotonic Dystrophy (MMD) and Oculopharyngeal Muscular Dystrophy (OPMD), Motor neuron diseases that can be treated include: Adult Spinal Muscular Atrophy (SMA), Amyotrophic Lateral Sclerosis (ALS), Infantile Progressive Spinal Muscular Atrophy (SMA, SMAL or WH), Intermediate Spinal Muscular Atrophy (SMA or SMA2), Juvenile Spinal Muscular Atrophy (SMA, SMA3 or KW) and Spinal Bulbar Muscular Atrophy (SBMA).

Diseases of the neuromuscular junction that can be treated include: Congenital Myasthenic Syndrome (CMS), Lambert-Eaton Syndrome (LES) and Myasthenia Gravis (MG).

Diseases of peripheral nerve that can be treated include: Charcot-Marie-Tooth Disease (CMT), Dejerine-Sottas Disease (DS), and Friedreich's Ataxia (FA).

Myopathies due to endocrine abnormalities that can be treated include: Hyperthyroid Myopathy (HYPTM) and Hypothyroid Myopathy (HYPOTM).

Other myopathies that can be treated include: Central Core Disease (CCD), Myotonia Congenita (MC), Nemaline Myopathy (NM), Myotubular Myopathy (MTM or MM), Paramyotonia Congenita (PC) and Periodic Paralysis (PP).

Metabolic diseases of muscle that can be treated include: Acid Maltase Deficiency (AMD), Carnitine Deficiency (CD), Carnitine Palmityl Transferase Deficiency (CPT), Debrancher Enzyme Deficiency (DBD), diabetes, Lactate Dehydrogenase Deficiency (LDHA), Myoadenylate Deaminase Deficiency (MAD) Mitochondrial Myopathy (MITO), obesity Phosphorylase Deficiency (MPD or PYGM), Phosphofructoldnase Deficiency (PFKM), Phosphoglycerate Kinase Deficiency (PGK) and Phosphoglycerate Mutase Deficiency (PGAM or PGAMM).

The polypeptide of the invention can also be used for treating or preventing congestive heart failure; for reducing frailty associated with aging; for increasing bone density (such as for treating osteoporosis) or accelerating bone fracture repair; for treating growth retardation, for the treatment of physiological short stature, for attenuating protein catabolic response such as after a major operation; for reducing protein loss due to chronic illness; for accelerating wound healing; for accelerating the recovery of burn patients or patients having undergone major surgery; for maintenance of skin thickness; for maintaining metabolic homeostasis, for treating renal failure/disease and liver failure/disease; for treating growth hormone deficient adults and for preventing catabolic side effects of glucocorticoids; and for treating a number of neuronal system disease conditions, including CNS injuries/disease such as spinal cord injury and stroke, and PNS injuries/diseases.

These disorders can be treated by administering a therapeutic amount of one or more myostatin antagonist to a subject in need thereof.

In a further embodiment, the invention contemplates the use of one or more muscle growth factors which may be co-administered with the pharmaceutical compositions of the present invention to give an additive or synergistic effect to the treatment regime. Such growth factors may be selected from the group consisting of HGF, FGF, IGF, MGF, growth hormone etc. Such growth factors may be administered either separately, sequentially or simultaneously with the pharmaceutical compositions comprising at least one polypeptide of the invention having myostatin antagonist activity.

In a further embodiment, the invention contemplates the use of a second pharmacologically active compound having different activity to the myostatin antagonist polypeptide of the invention to be used conjointly with the polypeptide of the invention to treat the myostatin related disorders. For example, the polypeptide may be administered in conjunction with active compounds selected from the group consisting of polypeptide growth factors (as mentioned above), NSAIDs or COX-2 inhibitors, alpha and beta blockers, ACE inhibitors, bisphosphonates, oestrogen receptor modulators, antihypertensive agents, glutamate antagonists, insulin, antibiotics, protein kinase C inhibitors or various over the counter substances as would be appreciated by a skilled worker. Such active compounds may be administered either separately, sequentially or simultaneously with the at least one polypeptide of the invention having myostatin antagonist activity.

The present invention is also directed to the use of one or more myostatin inhibitors in the manufacture of a medicament for treating myostatin related pathological conditions in a patient in need thereof. The one or more myostatin antagonists may be selected from the group of myostatin antagonists described above.

The medicament may be formulated for local or systemic administration. For example, the medicament may be formulated for injection directly into a muscle, or may be formulated for oral administration for systemic delivery to the muscle for the treatment of muscle wasting conditions. The medicament may be formulated for topical administration for the treatment of wound healing, and may be formulated for oral administration for the treatment of obesity and diabetes.

The medicament may further comprise one or more additional muscle growth promoting compounds to give an additive or synergistic effect to the treatment of muscle wasting conditions or for increasing muscle mass. The medicament may be formulated for separate, sequential or simultaneous administration of the one or more myostatin antagonists and the one or more muscle growth promoting compounds.

Without being bound by theory, it is thought that the novel polypeptides of the present invention, which have myostatin antagonistic activity, are effective at preventing or treating myostatin related disorders in part via three mechanisms. Firstly by inducing satellite cell activation, proliferation and differentiation. Satellite cells are the muscle stem cells and are thus involved in muscle tissue regeneration. Secondly, by enhancing myoblast proliferation and migration to the site of regeneration, and thirdly by enhancing macrophage recruitment. It is known that macrophages act to attract myoblasts and thus increase myogenesis. The effect on macrophage recruitment has previously been observed with other myostatin antagonists to result in improved wound healing (WO2006/083182). Thus, the present invention should also be effective at improving wound healing.

We show for the first time that novel myostatin inhibitors, comprising a C-terminally truncated mature myostatin peptide, wherein the C-terminal truncation is prior to amino acid 329, are useful in treating myostatin related disorders. In aged-related models of sarcopenia, the myostatin antagonists of the invention were effective not only at improving muscle mass and strength but also at reducing sarcopenia related fat depositions. These results were surprising given that the C-terminal truncation in these peptides was close to or excluded a cysteine resulting in the disruption of the three dimensional structure, a feature thought to be essential for biological activity (Jeanplong et al, 2001).

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Myostatin Antagonists Increase Myoblast Proliferation In vitro

Methods

Expression and Purification of Myostatin Antagonists

A cDNA corresponding to the 267-329; 267-320; 267-310; 267-300; and 267-280 amino acids of bovine myostatin sequence, hereafter referred to as myostatin antagonist 329, 320, 310, 300, and 280 respectively, was individually PCR amplified and cloned into apET16-B vector using BamHI sites. Expression and purification of myostatin antagonists 329, 320, 25 310, 300, and 280 was done according to the manufacturer's (Qiagen) protocol under native conditions yielding peptides with an N terminal (M G H H H H H H H H H H S S G H I E G R H M L E D P) and C terminal tag (E D P A A N K A R K E A E L A A A T A E Q).

Myoblast Assay

Bovine C2C12 myoblasts were grown in Dulbecco's modified eagle medium according to the standard techniques (Thomas et al, 2000). The myoblast proliferation assay was carried out in uncoated 96-well microtitre plates. C2C12 cultures were seeded at 1000 cells/well. Following a 16-hour attachment period, test media containing either recombinant wild type myostatin or different myostatin antagonists were added and cells were incubated for a further 48 or 72 hour period. For competition assay, wild type myostatin was competed with different concentrations of myostatin antagonists prior to the addition into the media. After the incubation period, proliferation was assessed using methylene blue photometric endpoint assay as previously described (Thomas et al, 2000).

Human skeletal muscle myoblasts (Cambrex, USA) or primary ovine myoblasts were grown in Dulbecco's Modified Eagle Medium containing 20% FBS, 10% Horse serum and 0.5% chicken embryo extract according to the standard techniques. The myoblast proliferation assay was carried out in uncoated 96-well microtitre plates. Cell cultures were seeded at 2000 cells/well. Following a 24-hour attachment period, test media supplemented with 5% FCS containing either buffer as a control or different myostatin antagonists (300, 310 or 320) were added at 1, 5 and 10 µg/ml and cells were incubated for a further 144 hour period (for human cells) or 48 hours (for ovine cells). After the incubation period, proliferation was assessed using methylene blue photometric endpoint assay as previously described (Thomas et al, 2000).

Results

Figure 29:
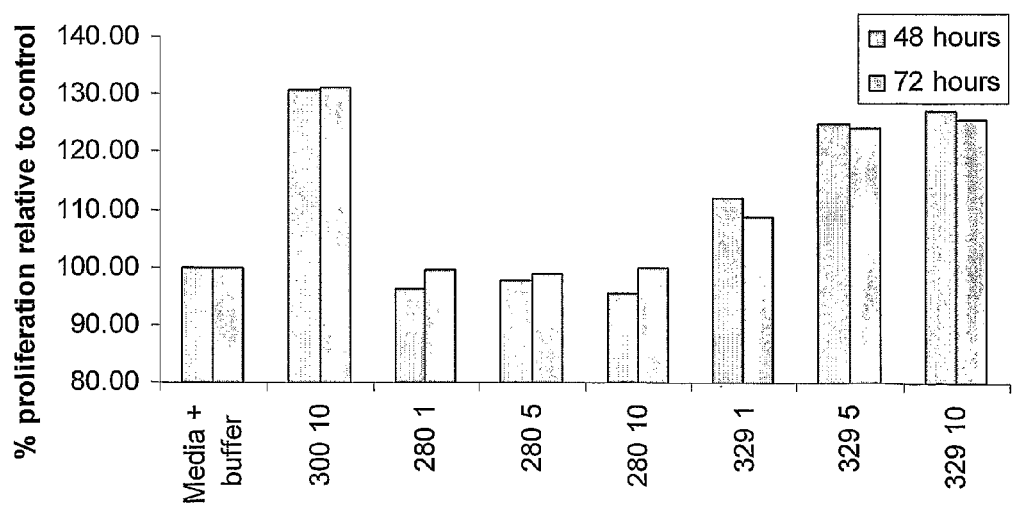

The results show that myostatin antagonists 300, 310, 320 and 329 significantly enhanced the proliferation capacity of myoblasts compared to control when present at 1 µg/ml or 5 µg/ml over 48 or 72 hours (FIG. 1 and FIG. 29). The highest myoblast proliferation rate was observed at the 48 hour time point for each of the 300, 310 and 320 antagonists when present at a concentration of 5 µg/ml and 10 µg/ml for 329. Myostatin antagonist 280 did not show activity above the control. This is likely due to the fact that this peptide contains only 1 cysteine residue.

Figure 2:
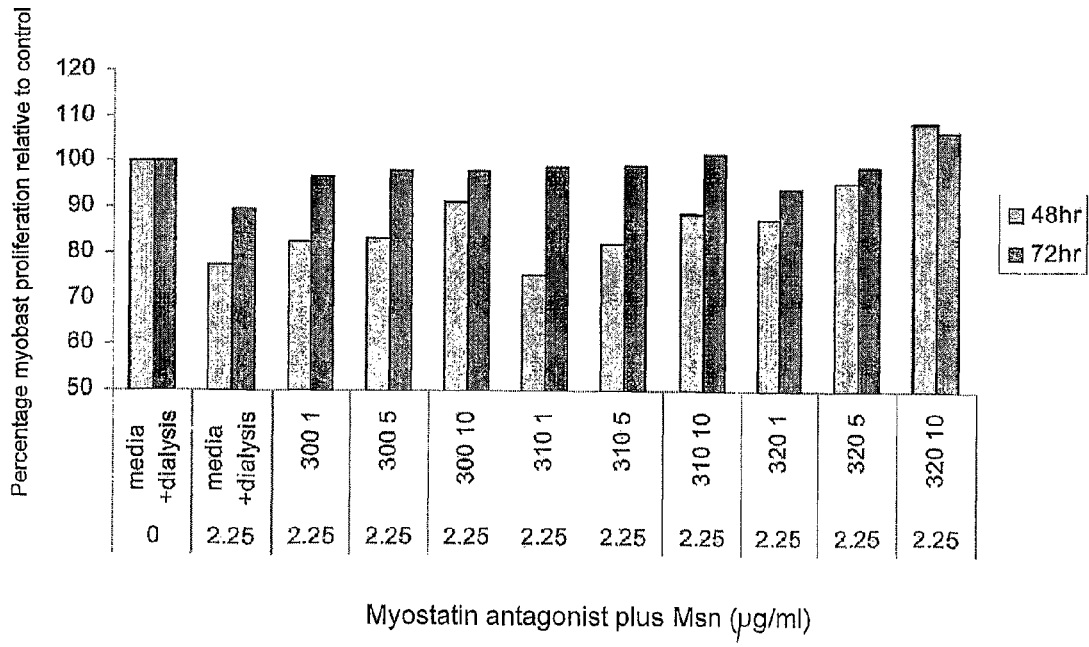
FIG. 2 shows the inhibitory effect of myostatin on C2C12 myoblast proliferation and recovery using myostatin antagonists 300, 310 and 320 at three concentrations (1, 5 and 10 µg/ml)

Addition of recombinant myostatin at 2.25 µg/ml to control medium led to a 25% inhibition of myoblast proliferation after 48 hours. This figure was reduced to about 10% after 72 hours (FIG. 2). When myostatin antagonists 300, 310 and 320 were added at three different concentrations (1, 5 and 10 µg/ml), the proliferation-inhibiting effects of myostatin on myoblasts was rescued to levels similar to those observed in the positive control. This demonstrated that myostatin antagonists such as 300, 310 and 320 can effectively accelerate muscle regeneration by enhancing myoblast proliferation (FIG. 2).

Figure 13:
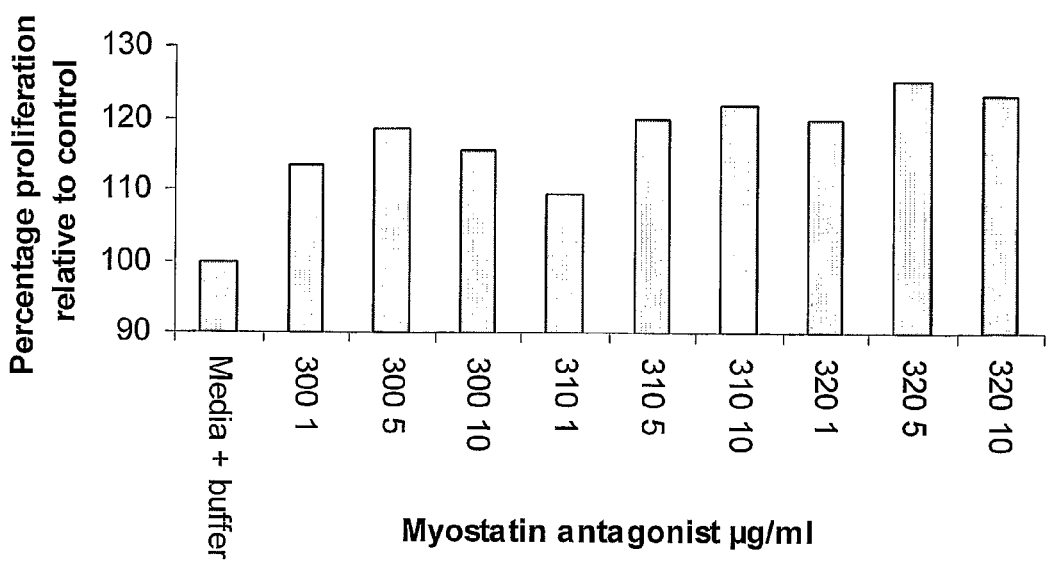
FIG. 13 shows the effect of myostatin antagonists 300, 310, and 320 (at 1, 5 and 10 µg/ml) on human myoblast proliferation. The myoblasts were cultured for 144 hours.
Figure 14:
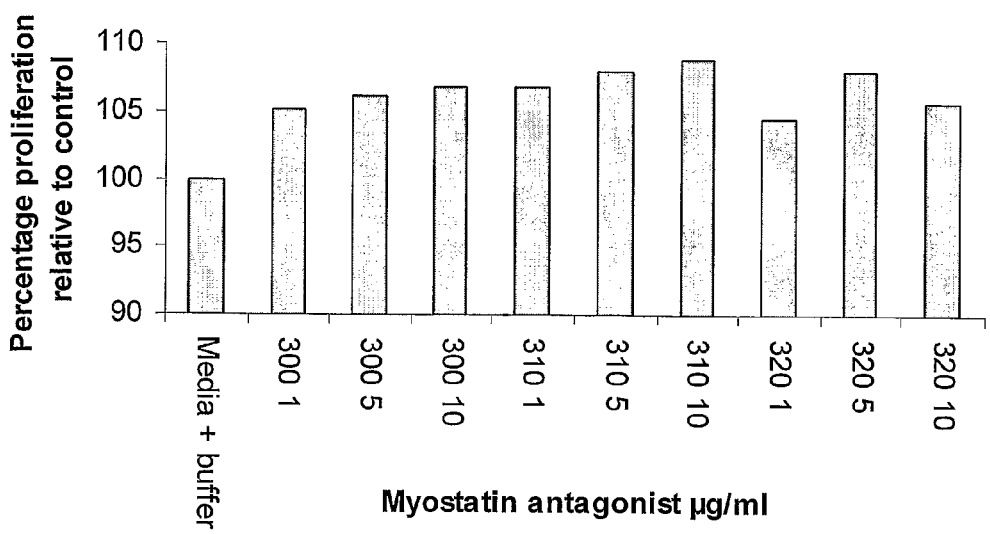
FIG. 14 shows the effect of myostatin antagonists 300, 310, and 320 (at 1, 5 and 10 µg/ml) on ovine myoblast proliferation. The myoblasts were cultured for 48 hours.

To determine whether the myostatin antagonists are effective in different species we conducted human and ovine myoblast proliferation assays. When myostatin antagonists 300, 310 and 320 were added at three different concentrations (1, 5 or 10 µg/ml over 48 or 144 hours) the proliferation capacity of human and ovine myoblasts was significantly enhanced when compared to control (FIG. 13 and FIG. 14).

These results indicate that administration of myostatin antagonists will have beneficial effects on patients suffering from muscle related disorders or any other disorders where an increased rate of proliferation of myoblasts is beneficial, such as in the treatment of muscle wasting disorders or regeneration of wounded muscle tissue.

Example 2

Myostatin Regulates Satellite Cell Activation

Methods
Single Myofibre Isolation and Culture

Single fibres were isolated as previously described Rosenblatt et al., (1995). Briefly, 1 and 24 month old wild-type mice were euthanized by $CO_2$ gas followed by cervical dislocation. TA were dissected out and digested in 0.2% (w/v) type 1A collagenase (>260 CDU/mg, Sigma) in Dulbecco's modified Eagle medium (DMEM) (Invitrogen) for 60 minutes at 37° C. Muscles were transferred to DMEM +10% horse serum (HS) +0.5% chicken embryo extract (CEE) and fibres were separated by gentle trituration. Isolated fibres were transferred to 4 well chamber slides (Becton Dickinson) coated with 10% matrigel (Becton Dickinson) and fixed with 100% ice cold methanol for 10 minutes after culturing up to 72 hours at 37° C. in 5% $CO_2$.

Proliferating Cell Nuclear Antigen (PCNA) is expressed in cells that are actively undergoing cell cycle but not in quiescent cells. A large percentage of the satellite cells attached to the muscle fibres are quiescent and hence do not express PCNA. However, upon activation, satellite cells are activated to express PCNA and regenerate the muscle by replenishing the muscle fibres. Thus PCNA is a very reliable antigen to marker for the activated satellite cells.

In order to determine the effect of myostatin antagonists on satellite cell activation, single muscle fibres from TA muscle of young (1 month) or old (24 month) wild type mice were cultured in presence of 5 µg/ml of myostatin antagonist 320, 310 or 300, in culture media for 24, 48 and 72 hours and fixed with methanol and washed in PBS. The fixed fibres were permeabilised in 0.5% TritonX-100 in PBS for 10 minutes, blocked in 10% normal goat serum and 0.35% carrageenan lambda in PBS for 30 minutes at room temperature then incubated with a 1:100 dilution of anti-PCNA antibody in blocker overnight. Primary antibody was detected using goat anti-mouse-alexa fluor 546 and fibres were counterstained with DAPI. PCNA positive activated satellite cells were counted under microscope and expressed as a percent of total myonuclei.

To test the effect of short term myostatin antagonist treatment on satellite cell activation, single fibres were isolated from mice from each treatment group (as described in example 4, below), and cultured as described above. Satellite cell activation was investigated using anti-PCNA antibodies as described.

Results
Myostatin Antagonists can Activate Satellite Cells

Figure 3:
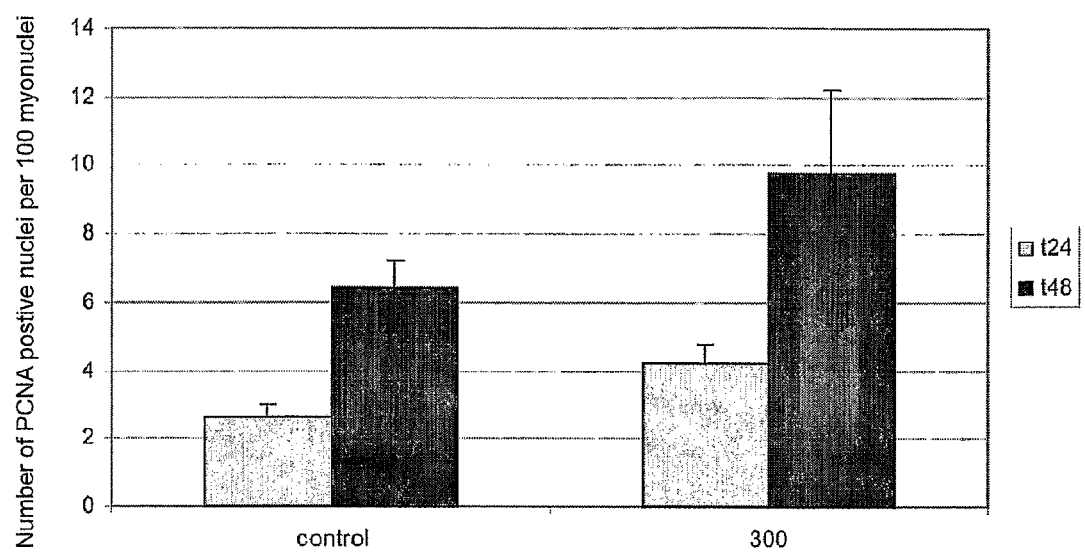
FIG. 3 shows the number of PCNA positive nucleic on isolated fibres from young (1 month old) wild-type mice. Isolated fibres were incubated with no antagonist (control) or with 5 µg of myostatin antagonist 300 for 24 or 48 hours.
Figure 4:
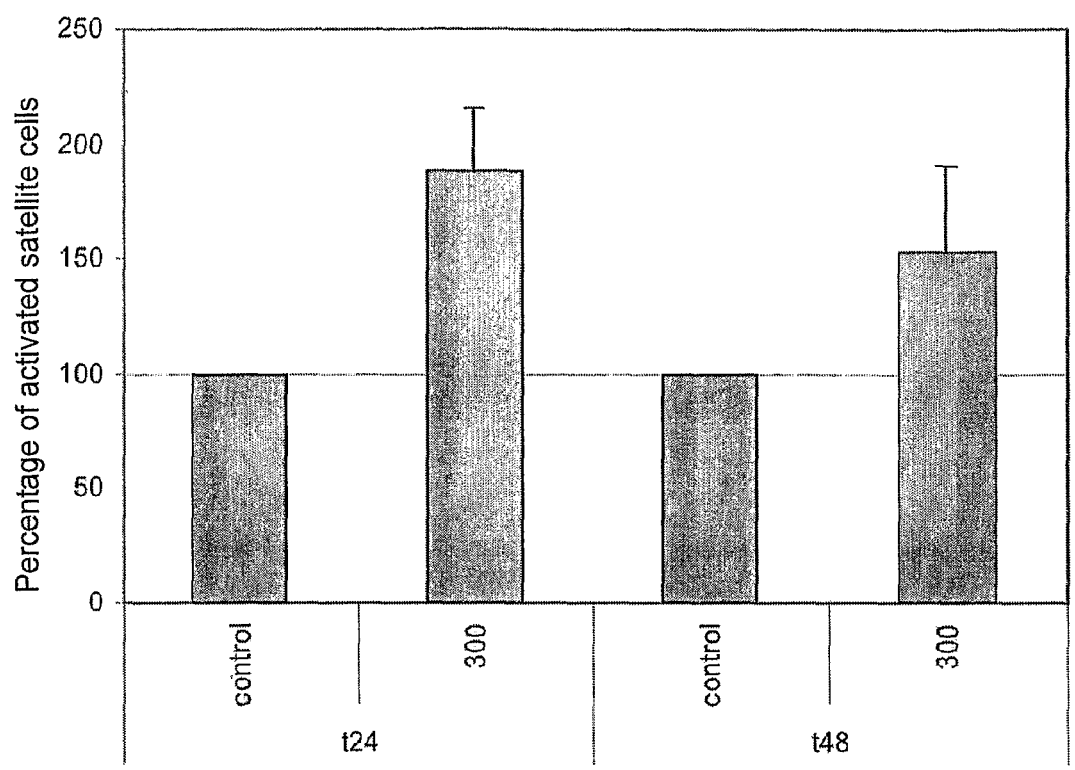
FIG. 4 shows satellite cell activation data from young (1 month old) wild-type mice. Isolated fibres were incubated with no antagonist (control) or 5 µg myostatin antagonist 300 for 24 or 48 hours. Activated satellite cells were detected by PCNA labeling through ICC. PCNA positive nuclei were counted per 100 myonuclei and raw data converted to percentage increases which were normalized to the controls. $*p=<0.05$.
Figure 5:
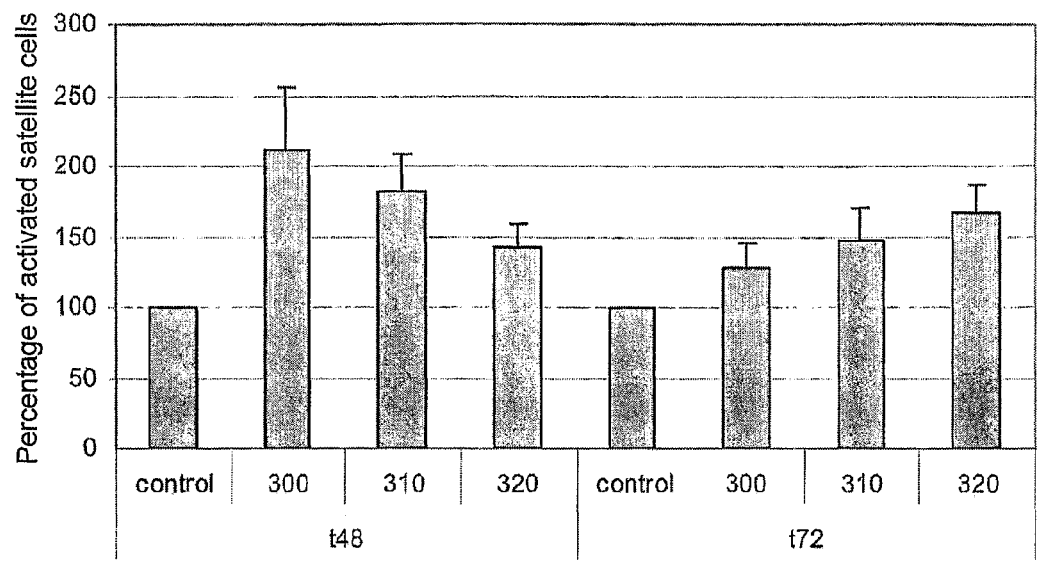
FIG. 5 shows satellite cell activation data from old (2 year old) wild-type mice. Isolated fibres were incubated with no antagonist (control) or 5 µg of myostatin antagonist 300, 310 or 320 for 24 or 48 hours. Activated satellite cells were detected by PCNA labeling through ICC. PCNA positive nuclei were counted per 100 myonuclei and raw data converted to percentage increases which were normalized to the control. $*p=<0.05$.

When single muscle fibres from young (1 month old) wild type mice were incubated with myostatin antagonist 300, a significant increase in the number of satellite cells activated was observed (FIG. 3). Similar results were seen when the number of activated cells were converted to a percentage increase, normalised against the controls (FIG. 4). This experiment was repeated using myostatin antagonists 300, 310 and 320 on single muscle fibres from old (2 year old) mice. Significant increases in the percentage of activated satellite cells were observed with all myostatin antagonists tested. The greatest increase was seen with myostatin antagonist 300 after 48 hours (FIG. 5). These results confirm that myostatin antagonists 300, 310 and 320 are potent activators of satellite cells in young and aged wild type muscle and indicate that administration of myostatin antagonists can be expected to treat or prevent the onset of disorders associated with a decrease in satellite cell activation such as sarcopenia. Furthermore it can be expected that myostatin antagonists may be used to reduce the severity of such conditions in cases where the proportion of activated satellite cells has already decreased. This data also shows that the antagonists are effective in increasing satellite cell activation in muscle fibres above normal levels of satellite cell activation. Therefore the myostatin antagonists could be used as a treatment prior to trauma due to medical treatments or prior to the onset of conditions that would be expected to result in decreased muscle strength such as enforced in activity or other conditions.

Example 3

Myostatin Antagonists Increase Inflammatory Response and Chemotaxis of Macrophages and Myoblasts Methods
Chemotaxis Assay Primary myoblasts were cultured from the hind limb muscle of young (4 to 6 week old) or old (24 month old) mice, according to the published protocols (Allen et al., 1997; Partridge, 1997). Briefly, muscles were minced, and digested in 0.2% collagenase type 1A for 90 min. Cultures were enriched for myoblasts by pre-plating on uncoated plates for 3 hours. Myoblast cultures were maintained in growth media (GM) supplemented with 20% fetal calf serum (FCS), 10% HS and 1% CEE on 10% Matrigel coated plates, at 37° C./5% $CO_2$. The extent of culture purity was assessed by flow cytometry analysis of MyoD expression after 48 hours in culture. Cells were harvested using trypsin, suspended at a concentration of $10^6$ cells/200 µl and fixed overnight in 5 ml 70% ethanol at −20° C. Staining was performed for 30 min at room temperature using rabbit polyclonal anti-MyoD, 1:200 (Santa Cruz), followed by Alexa fluor 488 anti-rabbit conjugate, 1:500 (Molecular Probes). Analysis was carried out in duplicate with $10^4$ cell events collected in each assay. Debris was excluded by gating on forward and side scatter profiles. Cells were analyzed by FACScan (Becton Dickinson). Macrophages were isolated by a peritoneal lavage technique and/or derived from bone marrow Zymosan-activated mouse serum (ZAMS) was prepared according to the published protocol (Colditz and Movat, 1984).

Figure 6:
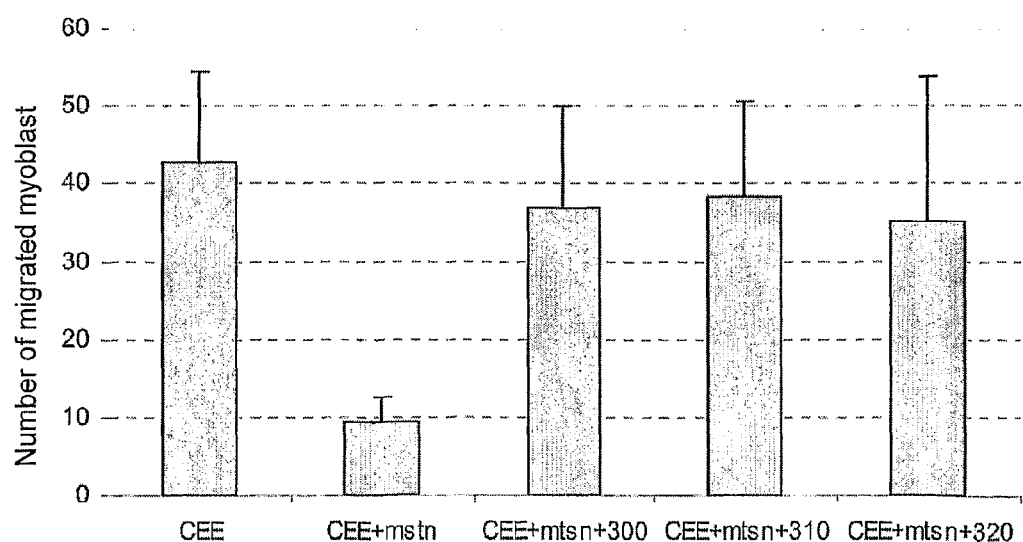
FIG. 6 shows the chemo-inhibitory effect of myostatin on primary myoblasts from old (2 year old) mice and recovery using myostatin antagonists 300, 310 or 320.

For the chemotaxis assay of myoblasts, a first assay was carried out on myoblasts from 2 year old mice as follows. DMEM containing 2% horse serum (HS), 5% chicken embryo extract (CEE) plus dialysis buffer was used as positive control. Recombinant myostatin (2.5 µg/ml myostatin) and myostatin antagonists 300, 310 and 320 (at 5-times myostatin concentration, i.e., 12.5 µg/ml) were added to positive control medium. Plain DMEM was used as negative control. On a 24-well plate, the bottom wells were filled with test or control media. Seventy-five thousand cells were added to the top wells containing polyethylene terephthalate (PET) 0.8 µm membranes coated with 1% Matrigel. The plate was incubated for 7 h at 37° C., 5% $CO_2$. The top surface of the membranes was washed with pre-wet swabs to remove cells that did not migrate. The membrane was then fixed, stained in Gill's hematoxylin and wet mounted on slides. Migrated cells were counted on four representative fields per membrane and the average number plotted. The results are shown in FIG. 6 (myoblast migration from old mice) and FIG. 7 (myoblast migration from young mice).

Figure 9:
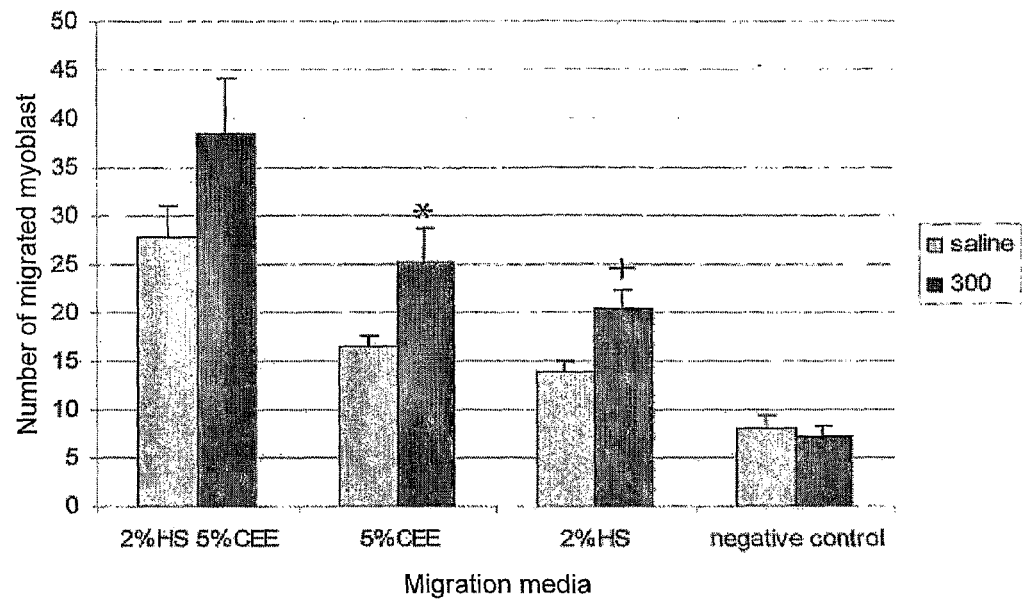
FIG. 9 shows the migration capacity of myoblasts derived from mice receiving saline (control) or myostatin antagonist 300 (6 µg/g body weight) three times per week for six weeks.

In a second myoblast migration assay, primary myoblasts isolated form hind limb of saline treated (control) and myostatin antagonist 300 treated mice (as described in example 4 below). Three chemo-attractant media were used: DMEM containing 2% horse serum (HS) and 5% chicken embryo extract (CEE) (optimal chemo-attractant); DMEM containing only 5% CEE or DMEM containing only 2% HS (both suboptimal chemo-attractants). Plain DMEM was used as negative control. On a 24-well plate, the bottom wells were filled with test or control media. Seventy-five thousand cells were added to the top wells. The plate was incubated for 7h at 37° C., 5% $CO_2$. The top surface of the membranes was washed with pre-wet swabs to remove cells that did not migrate. The membrane was then fixed, stained in Gill's hematoxylin and wet mounted on slides. Migrated cells were counted on four representative fields per membrane and the average number plotted. The results are shown in FIG. 9.

For chemotaxis analysis of macrophages bone marrow was isolated from saline treated (control) and myostatin antagonist 300 treated mice (as described in example 4, below), and plated at $5 \times 10^6$ cells/plate in DMEM 10% FBS plus 10% L929 conditioned medium (containing CSF-1) for 5 days to induce macrophage differentiation. The macrophages were then harvested and used in the assay. Three concentrations of DMEM containing Zymosan-activated mouse serum (ZAMS) was used, 33% (optimum chemo-attractant concentration), 22% and 11% (suboptimal chemo-attractant concentrations). Plain DMEM was used as negative control. On a 24-well plate, the bottom wells were filled with test or control media. Seventy-five thousand cells were added to the top wells containing polyethylene terephthalate (PET) 0.8 µm membranes. The plate was incubated for 4h at 37° C., 5% $CO_2$. The top surface of the membranes was washed with pre-wet swabs to remove cells that did not migrate. The membrane was then fixed, stained in Gill's hematoxylin and wet mounted on slides. Migrated cells were counted on four representative fields per membrane and the average number plotted.

Results

Figure 7:
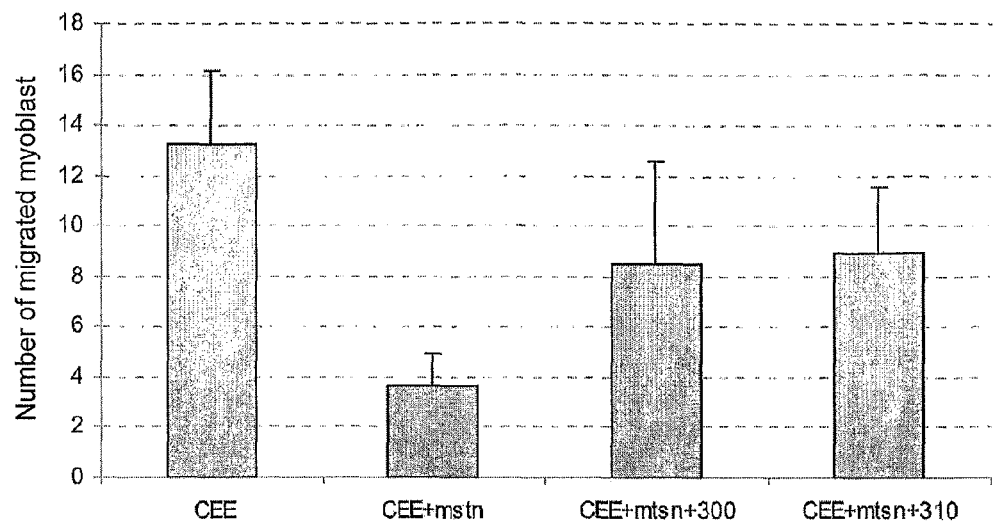
FIG. 7 shows the chemo-inhibitory effect of myostatin on primary myoblasts from young (1 month old) mice and recovery using myostatin antagonists 300 and 310.
Figure 8:
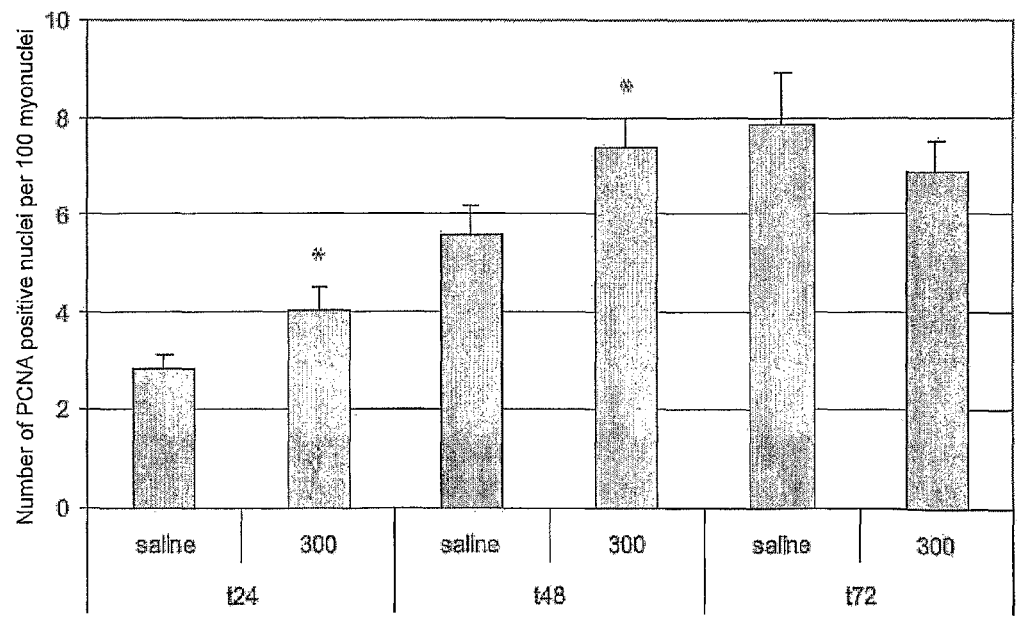
FIG. 8 shows the satellite cell activation data from mice receiving saline (control) or myostatin antagonist 300 (6 µg/g body weight) three times per week for six weeks.

When primary myoblasts isolated from old (2 year old) mice were incubated with recombinant myostatin at 2.5 µg/ml in control (CEE) medium, a significant decrease of approximately 78% was seen in the number of migrated myoblasts. When myostatin antagonists 300, 310 and 320 were added at 5 µg/ml, the chemo-inhibiting effects of myostatin on myoblast migration was rescued to levels similar to those observed in the control (FIG. 6). This experiment was repeated using myoblasts from young (1 month old) mice. Again, addition of myostatin antagonists 300 and 310 to myostatin containing media rescued the migration of myostatin cells to control levels (FIG. 7). These results demonstrate that myostatin antagonists such as 300, 310 and 320 can effectively accelerate muscle regeneration by enhancing myoblast migration. As shown above, myostatin has a negative effect on myoblasts accretion to the wounded area. Since myoblasts are known to be influenced by chemotactic factors to direct their movement (Bischoff, 1994; Jones, 2000), the effect of in vivo administration of myostatin antagonist 300 on the migratory ability of satellite cell derived myoblasts was investigated using three chemo-attractants. Myoblasts isolated from mice that had been treated with myostatin antagonist 300 had significantly increased migration rates in each chemo-attractant media compared to macrophages isolated from saline treated control mice (FIG. 9).

Figure 10:
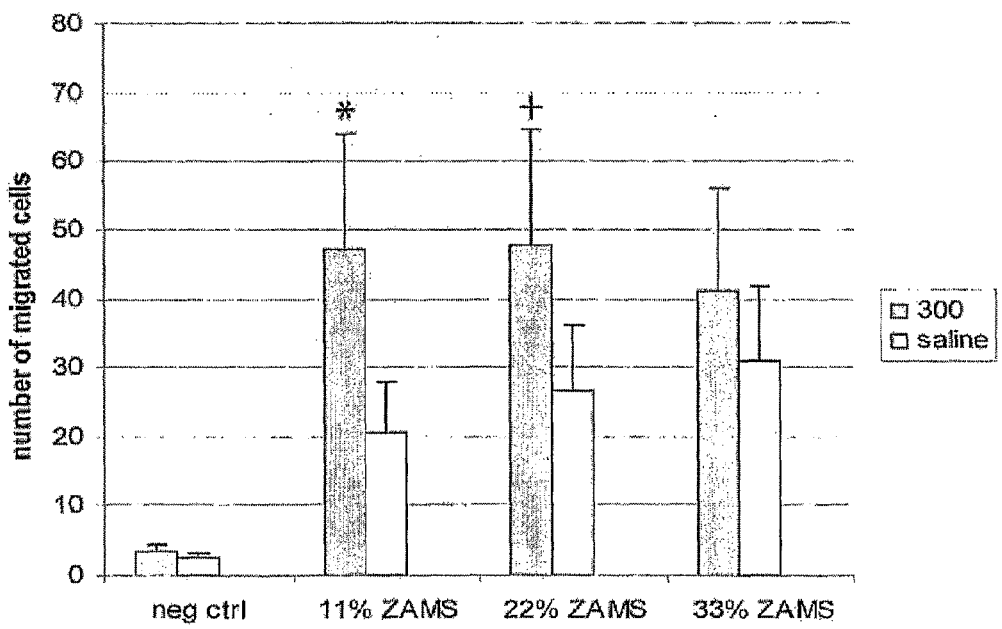
FIG. 10 shows the migration capacity of bone marrow derived macrophages from mice receiving saline (control) or myostatin antagonist 300 (6 µg/g body weight) three times per week for six weeks.

It is also known that myostatin has an effect on the inflammatory response, in particular, myostatin interferes with the migration of macrophages to the site of injury during muscle regeneration. To assess whether or not treatment with myostatin antagonist 300 in vivo affected the migration of macrophages, an in vitro migration assay was carried out on macrophages isolated from mice treated with saline (control) or antagonist 300 for six weeks. The results showed that antagonist 300 in vivo treatment significantly increased the migratory ability of macrophages in three different concentrates of chemo-attractant media ZAMS (11%, 22% or 33%) compared to macrophages isolated from saline treated controls (FIG. 10).

The ability of in vivo administration of myostatin antagonist 300 to enhance the migration rate of both myoblasts and macrophages indicates that administration of myostatin antagonists could be used as an effective treatment in patients suffering from conditions where inhibition of myostatin activity would be clinically beneficial, including muscle wasting conditions and inflammatory myopathies, as well as being useful for wound healing and any other pathologies where enhanced migration of macrophages and myoblasts can confer benefits.

Example 4

In vivo Trials with Myostatin Mimetic 300

Methods

An animal trial was conducted to assess the effects of myostatin antagonist 300 in improving muscle function. Sixteen month old mice were divided into two groups of ten. While the control group received saline subcutaneous (SC) injections, the other group received myostatin antagonist 300 SC at 6 µg/gram of BW three times a week for six weeks. The functional improvement of sarcopenic muscle was assessed by measuring grip strength of mice at the end of trial. Grip strength was measured in Newtons.

Results

Figure 11:
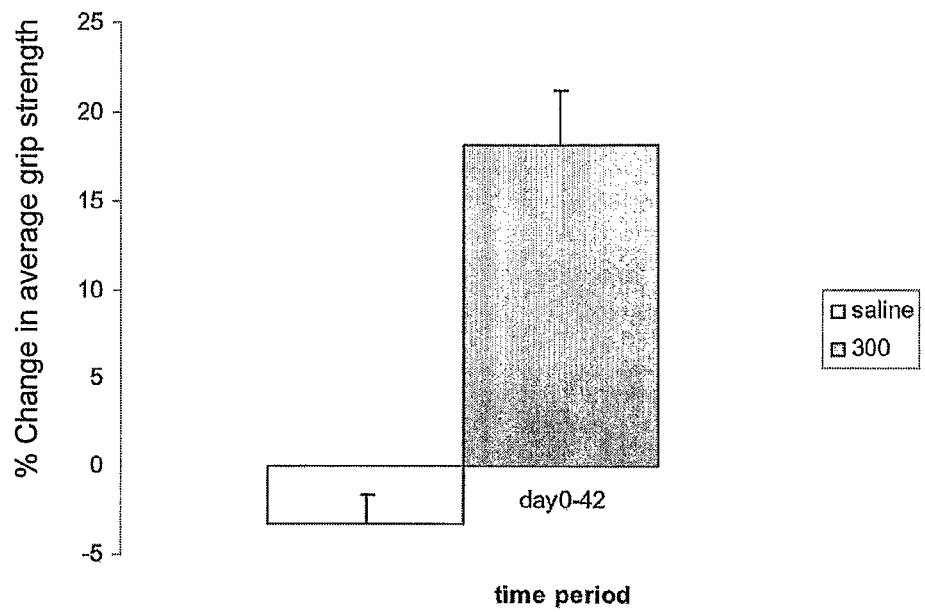
FIG. 11 shows the average percent change in grip strength in mice receiving saline (control) or myostatin antagonist 300 (6 µg/g body weight) three times per week for six weeks.
Figure 12:
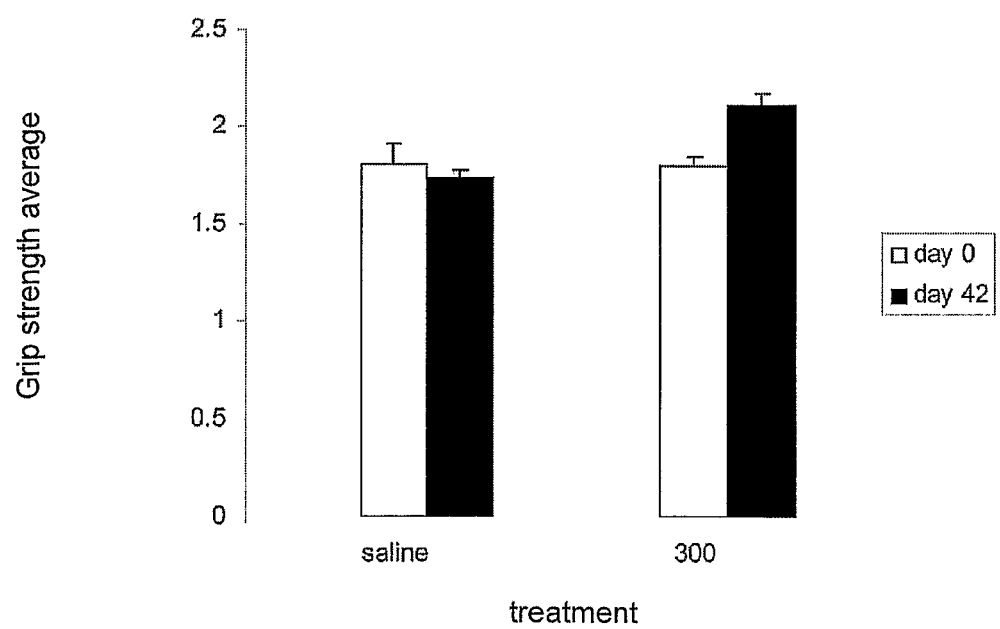
FIG. 12 shows the average grip strength of the control and treated mice of FIG. 11 at day 0 and day 42.

The results indicate that while there is a reduction in the grip strength of the control mice (loss of ~5%), there is highly significant increase in the grip strength of aged mice treated with the 300 antagonist over a six week period (FIG. 11). The same data was expressed as grip strength at the beginning and end of the trial for both groups (FIG. 12), and the same observation was made in which grip strength was significantly increased in mice treated with the myostatin antagonists 300. This was due in part to the increase observed in satellite cell activation and macrophage and myoblast migration obtained in cells and fibres isolated from these mice at the end of the treatment period (FIGS. 9 and 10).

An additional important observation was noted. At 16 months, aged wild-type mice showed significant accumulation of body fat. In both treatment groups, all mice were observed to have a distinct reduction in body fat compared with the saline treated controls. This was very noticeable. It thus appears that prolonged treatment with myostatin antagonists seems to have reduced the amount of subcutaneous fat including the inguinal fat pad in the mice treated with 300 when compared to the control mice (result not shown).

It has previously been shown that deletion of myostatin during embryonic stages affects postnatal fat accumulation. However the surprising result here is that treatment of mice for a 6 week period has reduced the amount of fat tissue. This could be due to the myostatin antagonists either mobilizing the triglycerides stored in the adipose tissue interfering with fatty acid biosynthesis or another mechanism. Regardless, this experiment clearly exemplifies the control of fat tissue size by the myostatin antagonists as opposed to the lean body mass due to a complete absence of myostatin (myostatin null mice) right from embryonic stages.

It thus appears that myostatin antagonists are useful in not only treating or preventing the reduction in muscle mass and strength induced by sarcopenia but are also useful in reducing the increased fat deposition that is also associated with old age. In addition, it is envisaged that the myostatin antagonists of the present invention will have utility in controlling/reducing the amount of fat tissue in clinical conditions of obesity, anorexia and diabetes.

Example 5

Mdx In Vivo Trial

Methods:

An in vivo trial was performed in which 4 week old mdx mice were injected 3× per week with 300 (6 µg/g) or saline (10 mice in each treatment) for 4 weeks. Body weights were recorded regularly and blood was collected for creatine kinase activity to assess the extent of muscle damage. Grip tests were performed as a measure of strength. After 4 weeks of treatment mice were culled and individual hind limb muscles collected for protein expression analysis—Pax7 & MyoD (satellite cell activation/myogenesis), and histology.

Protein was extracted from three hind limb muscles, biceps femoris, tibialis anterior and gastrocnemius. 15 µg of protein was separated on 4-12% SDS PAGE, transferred to nitrocellulose membrane and immunoprobed with Pax7 and MyoD.

Ten micron transverse sections were cut from the midbelly region of each m. gastrocnemius. Muscle sections were stained with haematoxylin and eosin (H & E) to visualise and measure areas of necrosis and regeneration. These areas were analysed using an Olympus BX50 microscope (Olympus, Tokyo, Japan), a SPOT-RT 4.01 camera and software (Diagnostic Instruments, Sterling Heights, Mich.). Areas were measured using Image-Pro Plus (Media Cybernetics, Silver Spring, Md.).

Blood was collected by tail-bleeding into 75 mm heparinised microhematocrit tubes. Tubes were centrifuged in a Micro-hematocrit centrifuge (Adams) for 5 minutes and then the plasma removed. The recovered plasma was centrifuged again at 2500×g for 5 minutes and then stored at −80° C. until analysis. Plasma was separated from the red blood cells within 2 hours of blood collection to minimise hemolysis.

Creatine kinase activity was determined using CK N-acetyl-L-cysteine creatine kinase kit (Beckman Coulter) within 6 weeks of plasma collection. Muscle strength was assessed using a grip strength apparatus (MK-380S, Muromachi; Tokyo, Japan) at the beginning, mid-point and end of the trial. The maximum force exerted by a mouse while being pulled backward by the tail is recorded in Newtons. The mean of three grip tests for each mouse was calculated and the mean maximal force of 10 mice per group was determined.

Results

MyoD and Pax7 are Upregulated in Response to 300 Treatment.

Both Pax7 and MyoD have been established as potent markers of myogenesis. Pax7 levels indicate the extent of satellite cell pool as well as satellite cell self-renewal and MyoD expression indicates the level of myogenesis occurring within a muscle. To investigate Pax7 and MyoD protein levels in the muscles of mdx mice, western blot analyses were performed.

Figure 15:
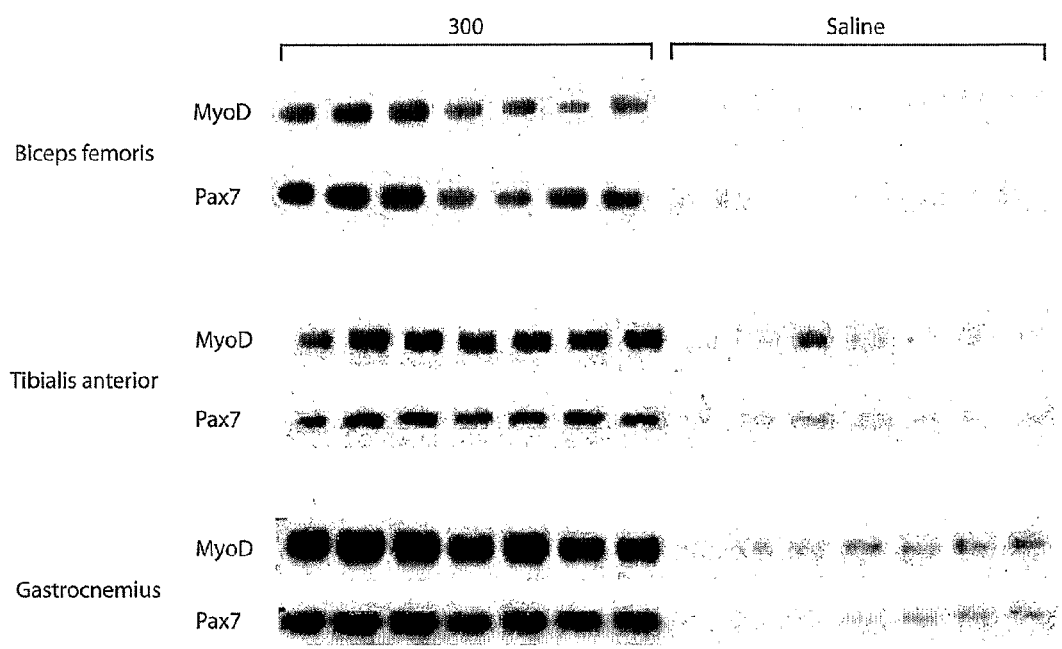
FIG. 15 shows that MyoD and Pax7 are upregulated in biceps femoris, tibialis anterior and gastrocnemius muscles following myostatin 300 antagonist treatment in mdx mice.

As shown in FIG. 15 there was a substantial upregulation of both Pax7 and MyoD. Pax7 is expressed in both quiescent and proliferating satellite cells. The upregulation of Pax7 is indicative of increased activation of satellite cells, higher satellite cell number and increased satellite cell self renewal. MyoD is an important myogenic gene and its upregulation is indicative of an increase in myogensis via upregulation of p21 and Myogenin. The upregulation of both Pax7 and MyoD suggests that 300 effectively antagonises myostatin as it is well established that absence of myostatin leads to increased satellite cell activation and self renewal and myogenesis.

Reduced Necrosis and Increased Regeneration is Observed in 300 Treated Muscles.

Figure 16:
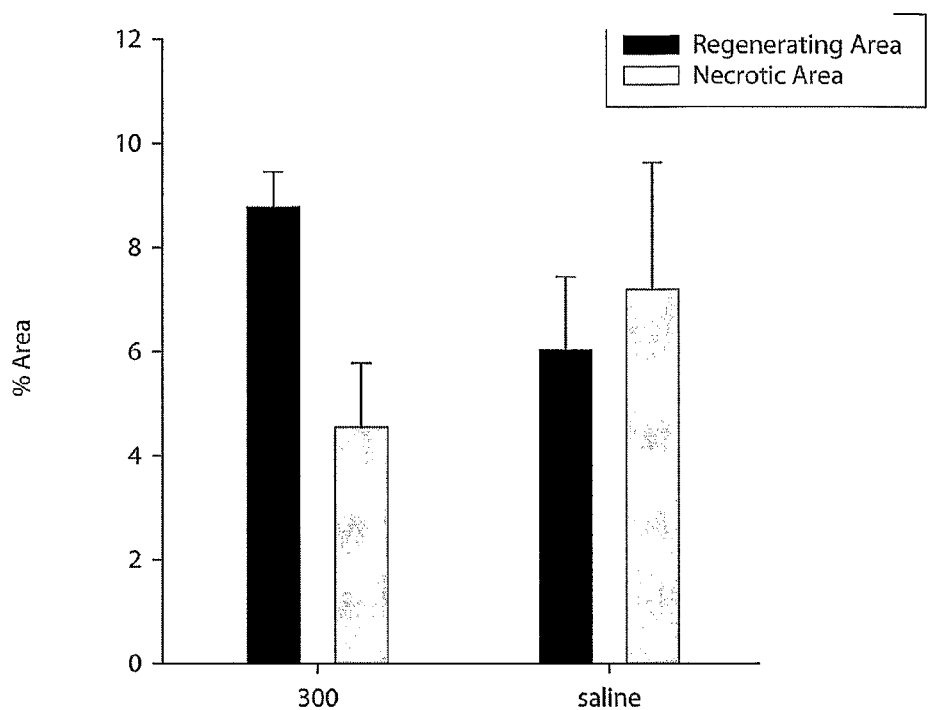
FIG. 16 shows that antagonism of myostatin with 300 enhances muscle regeneration and reduces necrosis in mdx mice.
Figure 17:
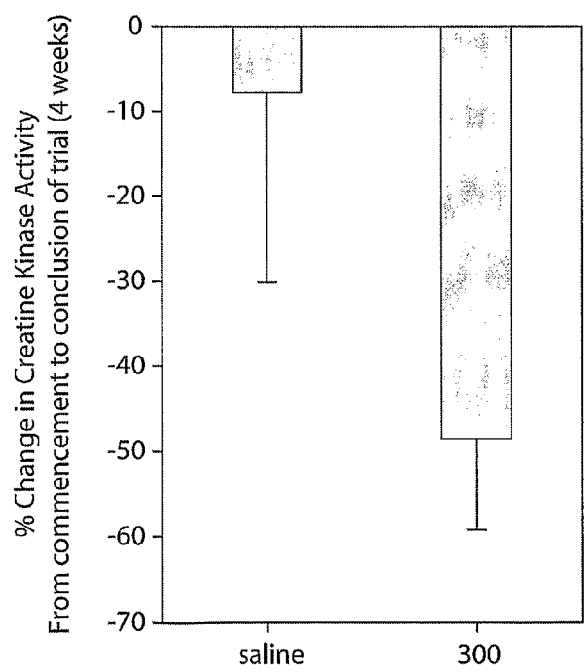
FIG. 17 shows that antagonism of myostatin with 300 decreases creatine kinase activity in mdx mice.

The percentage area of regenerating and necrotic areas are shown in FIG. 16. This result is consistent with the hypothesis that myostatin antagonists increase muscle regeneration and repair by activating satellite cells thereby increasing the formation of new muscle fibres and decreasing levels of necrotic tissue as also indicated by the enhanced MyoD and Pax7 expression and reduced CK values in the blood (FIG. 17).

Creatine Kinase Activity is Reduced in Mice Treated with Inyostatin 300.

Creatine kinase (CK) is an intracellular enzyme commonly used as a primary marker to monitor extent of muscle damage in mdx mice (Bogdanovich et al., 2005) and humans. The change in creatine kinase activity from the commencement to the completion of the trial is shown in FIG. 17. The larger decrease in creatine kinase activity in the 300 treated mice suggests less muscle damage in these animals due to a change in the proportion of muscle cells regenerating versus damaged or necrotic state. This corroborates the histological data showing less necrotic area in 300 treated mice Antagonism of Myostatin with 300 Increases Grip Strength.

Figure 18:
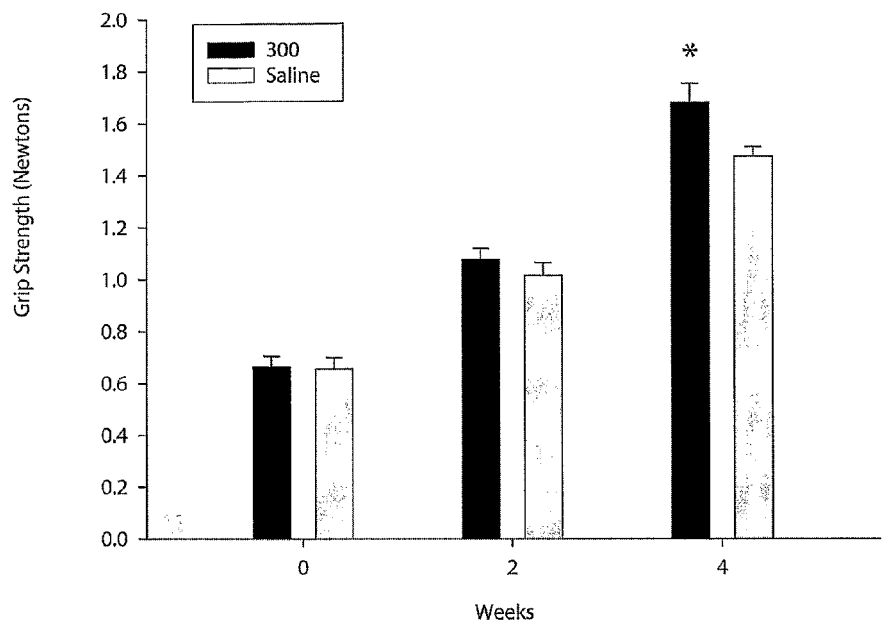
FIG. 18 shows that antagonism of myostatin with 300 increases grip strength in mdx mice.

The mean of three grip tests for each mouse was calculated and the mean maximal force of 10 mice per group is shown in FIG. 18. The significant increase in grip strength after 4 weeks of 300 treatment indicates a functional improvement in the 300 treated mice. We largely attribute this to the amelioration of the pathology of mdx mice muscles through increased regenerative effects, via antagonism of myostatin resulting in a partial recovery of muscle function. These findings suggest that beneficial effects of myostatin antagonists in mdx mice are likely to be due to effective treatment of muscle damage enabling a rescue of grip strength in mdx back to wild type (Amthor et al., 2007).

Example 6

In vivo Skin Biopsy Trial

Methods:

C56b1/6 mice at ~10 months of age were anesthetized, the skin at the back of the neck was shaved, and two wounds made on the skin with a 4 mm biopsy punch. The mice were injected subcutaneously with either saline or 300 myostatin antagonist at 6 µg/g of body weight at day 1, 3, 5 and 7 after injury. The mice were allowed to heal for 5, 7, 14, 21 and 28 days, after which they were culled and the skin processed for histology.

For the histology, skin samples were fixed in 10% formalin, embedded and mounted in paraffin and stained with Masson's Trichrome stain. The sections were analysed for the size of wound area for each day following the treatments, and the values plotted.

Figure 20:
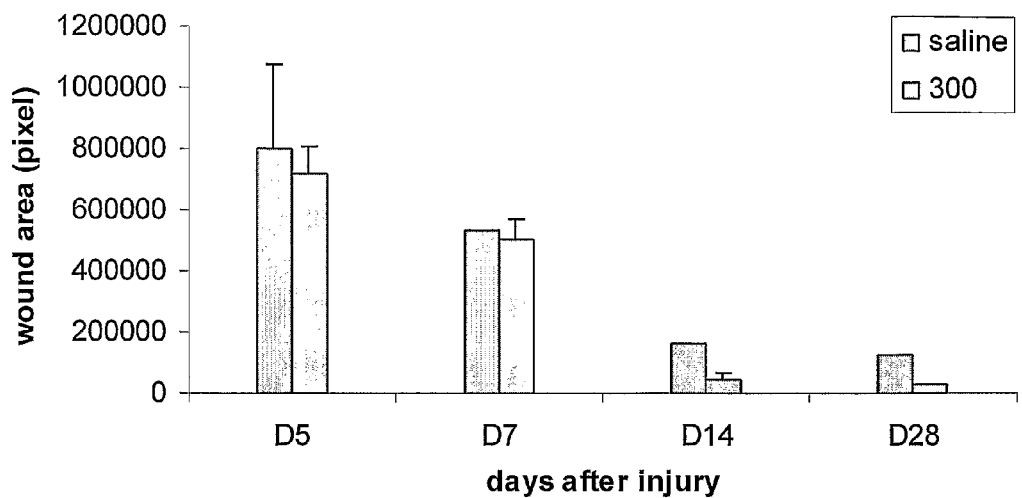
FIG. 20 shows an increased wound healing in mice after skin biopsy when treated with myostatin antagonist 300.

Results:

To evaluate the impact of myostatin antagonism in wound healing in skin we performed a skin biopsy study in mice. Animals treated with 300 consistently showed smaller wound area when compared with the saline counterpart, particularly at the later time points as shown in FIG. 20 indicating that treatment with 300 antagonist can positively influence the rate of skin healing in mice following a biopsy wound. This result shows that antagonism of myostatin can confer improved rates of healing in a non-muscle tissue such as skin and indicates that the use of myostatin antagonists has applications in improving healing of skin after damage from wounds, burns, surgical incisions and other skin traumas.

Example 7

In vivo Skin Burn Trial

Methods:

C56b1/6 mice at ~12 months of age were anesthetized, the skin at the back of the neck was shaved, and a red-hot metal rod (1.5 mm wide, 7 mm long) was applied to the exposed skin of the mice for 5 sec. The mice were injected subcutaneously with either saline or 300 myostatin antagonist at 6 µg/g of body weight at day 1, 3, 5, 7 and 10 after injury. The mice were allowed to heal for 5, 7, 14, 21, 28, 35 and 46 days, after which they were culled and the skin frozen in liquid nitrogen for hydroxyproline analysis.

Figure 21:
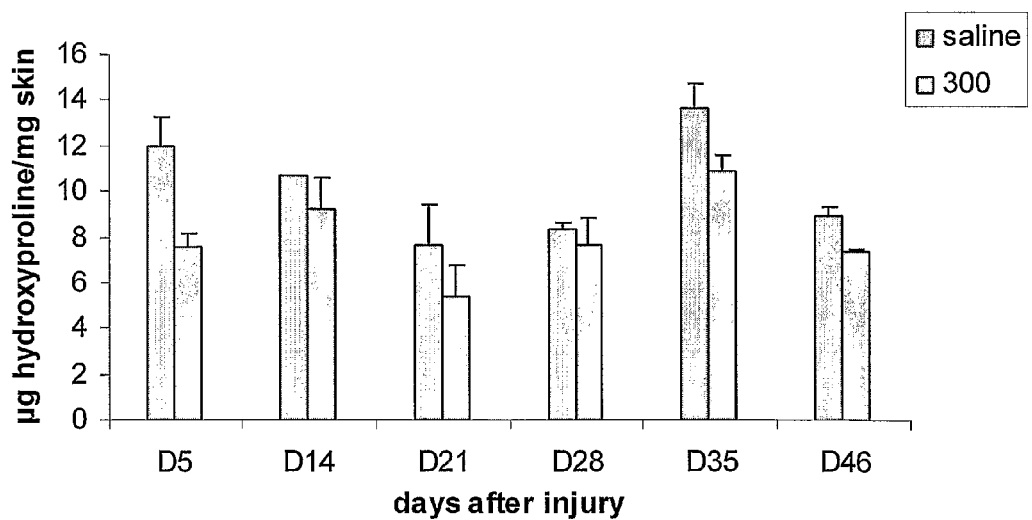
FIG. 21 shows the collagen deposition on the wound area in mice after skin burn with and without treatment with 300.

Results:

After a burn injury in skin a hydroxyproline assay was performed to determine the amount of collagen deposits on the wound area. Hydroxyproline is present in collagen, and gives it a stable helical conformation. Therefore, measuring the amount of hydroxyproline present in a given tissue will determine the amount of collagen present in the tissue. The 300 treated groups showed a tendency towards lower level of collagen on the wound area when compared with the control group as shown in FIG. 21 suggesting that the myostatin antagonists could be useful in the treatment of non-muscle tissue where the desired outcome is decreased fibrosis after wound healing.

Example 8

In vivo Muscle Burn Trial

Methods:

C56b1/6 mice at ~12 months of age were anesthetized and a red-hot metal rod (1.5 mm wide, 7 mm long) was applied to TA muscle for 5 sec. The mice were injected subcutaneously with saline or 300 myostatin antagonists at 6 µg/g of body weight at day 1, 3, 5, 7 and 10 after injury. The mice were allowed to heal for 5, 7, 14, 21, 28, 35 and 46 days, after which they were culled and the muscle processed for histology.

Histological muscle samples were covered in OCT and frozen in isopentane cooled in liquid nitrogen. The sections were cut in a cryostat at 10 µm thickness and stained with H&E and Van Gieson. Regeneration markers such as total number of centrally formed nuclei (CFN) and number of fibres with CNF were analysed for each day following the different treatments, and the values plotted.

Figure 22:
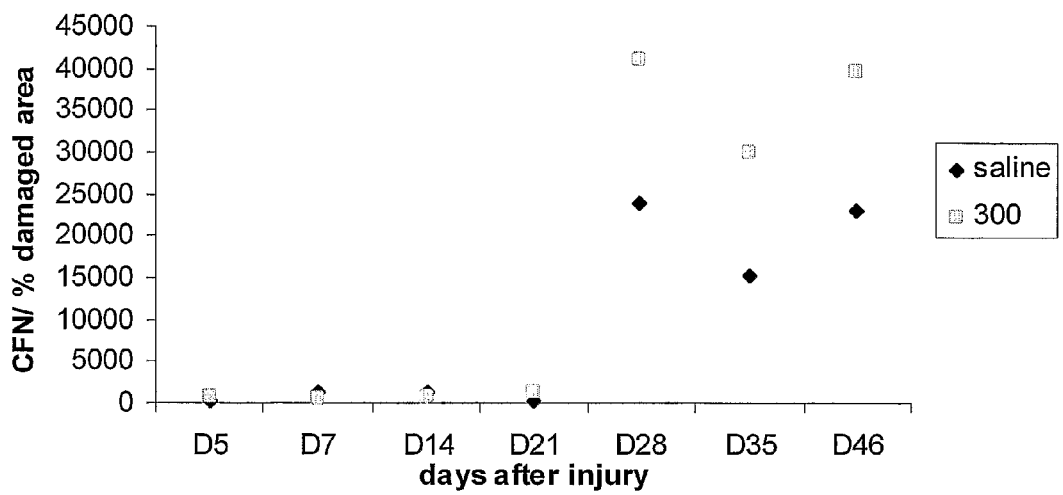
FIG. 22 shows increased number of myogenic markers (total number of centrally formed nuclei (CFN)) after muscle burn when treated with 300 as compared to saline.
Figure 23:
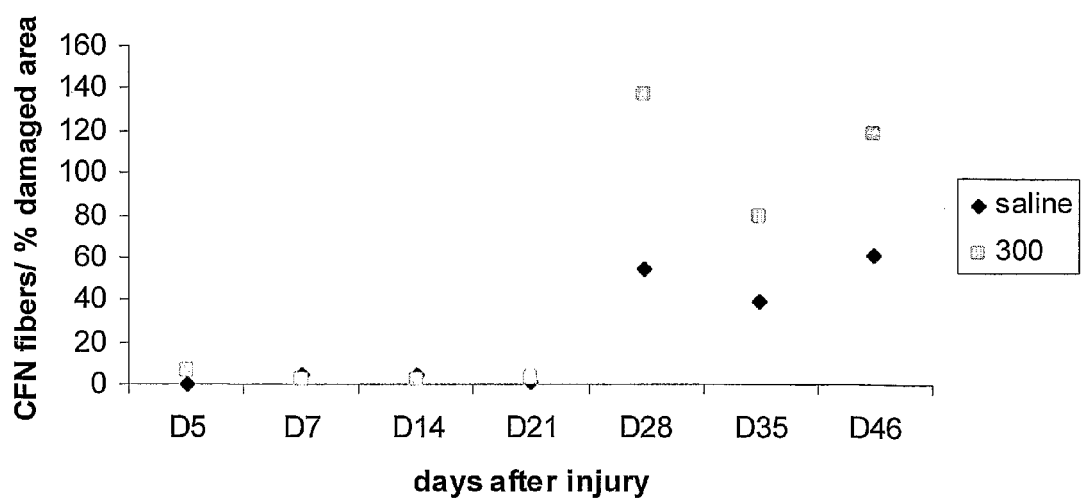
FIG. 23 shows increased number of myogenic markers (number of fibres with centrally formed nuclei (CFN)) after muscle burn when treated with 300 as compared to saline.
Figure 30:
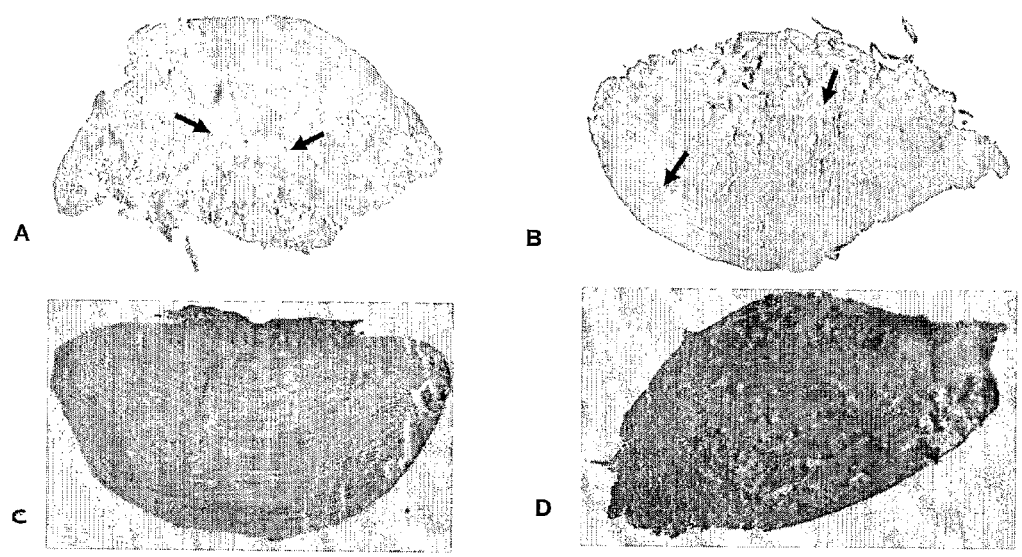
FIG. 30 A (control) and B (300 treated) show van Giesen staining of the muscle 21 days after burn injury, in which the arrows indicate collagen deposits on muscle, i.e., formation of fibrotic tissue on muscle. Saline treated muscle (control) shows a higher amount of collagen deposit when compared to 300 antagonist treated muscle.

Results:

Mature skeletal muscle fibers have nuclei located at the periphery of the fiber. However, during skeletal muscle regeneration, myoblasts migrate to the site of injury and fuse to pre-existing fibers or fuse to each to form nascent myofibers. During this process the nuclei of these cells are located in the center of the fiber. We therefore used the number of centrally formed nuclei (CFN) and the number of fibers with CNF as markers of muscle regeneration. The damage present in the muscles for the first time points of the trial was too widespread, and no positive regeneration marker was detected for either the treated or control group (FIG. 22 and FIG. 23). However, by D21 the numbers of CFN in treated groups is significantly higher than that in control groups indicating increased muscle regeneration on the treated animals. This difference is maintained up to day 46 after injury. Interestingly, there is no difference in the percentage of damage muscle area between the treatment and control groups from D28 onwards (data not shown). This indicates that the increase in regeneration in the 300 treated groups as shown in the increased numbers of CNF resulted in an improvement in muscle regeneration after burning. Furthermore, visually, differences in muscle fibre integrity between the treated and control groups can be seen from D21 onwards in the treatment group. Also, van Gieson staining revealed a higher degree of fibrosis in the control group when compared to the treated groups at D21 after injury (FIG. 30) signifying earlier remodelling of the injured area, and therefore an earlier influx of myogenic precursors, leading to the increase CFN seen from D28 onwards between the treated and control groups. Decreased fibrosis per se is also attributed to the effects of the myostatin antagonist on the extent of fibrosis that occurs during repair of wounded tissues.

Example 9

In vitro Cancer Cachexia Trial

Methods:

C2C12 cells were differentiated for 72 hours in differentiation media (DMEM+2% HS). Following this period of differentiation the myotubes were tested with recombinant myostatin at 6 µg/mL or a combination of both myostatin and 300 recombinant protein at 30, 60, 90 or 120 µg/mL for further 24 hours to determine if 300 can rescue myostatin-mediated muscle wasting in vitro. Gene expression changes of intermediate signalling molecules critical in myostatin-mediated cachexia were analysed. Therefore, protein was isolated from cells and Western blot analysis was performed to measure protein expression levels for p-FoxO1, which we have shown to be a critical signalling intermediates in Myostatin-mediated cachexia (McFarlane et al 2006).

Results:

p-FoxO1 is a critical intermediate signalling molecules in myostatin mediated cachexia. In the experiment expression levels of p-FoxO1 were normalised to total levels of FoxO1.

Figure 24:
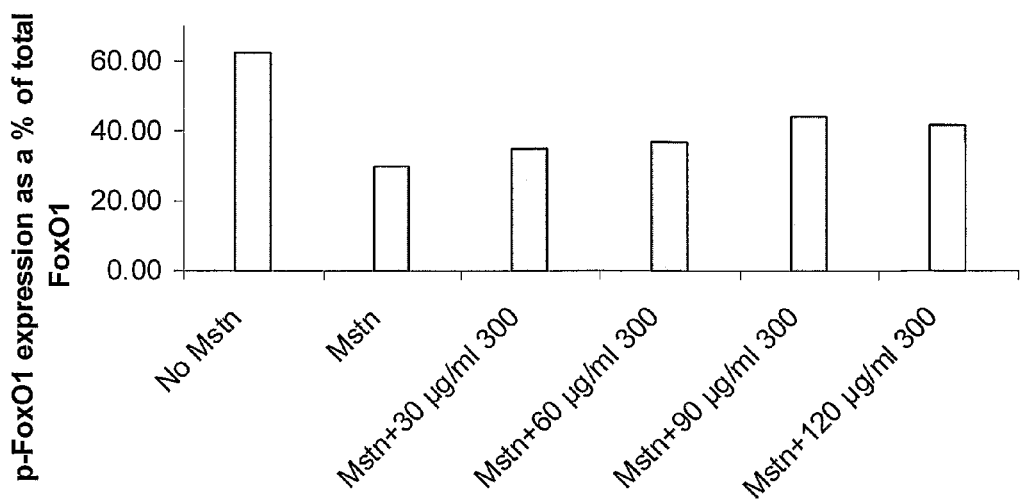
FIG. 24 shows that antagonism of myostatin with 300 rescues the expression of p-FoxO1 after inhibition with myostatin.

As shown in FIG. 24, treatment with 6 μg/mL recombinant Myostatin protein results in down-regulation of p-FoxO1 expression following a 24 hour treatment. This result is consistent with our previously published data describing the mechanism behind Myostatin-mediated cachexia (McFarlane et al., 2006). A maximal rescue of p-FoxO1 expression is obtained with 90 μg/mL 300 (FIG. 24). This shows that application of the 300 myostatin antagonist can reduce the magnitude of the FoxO1 signal that is critical in a proportion of cachexic wasting conditions.

Example 10

In vivo Cancer Cachexia Trial

Methods:

A study of chronic cachexia was designed whereby C57B mice, 4 weeks of age, were injected with the glucocorticoid drug Dexamethasone daily at a concentration of 1 mg/kg body weight. Three treatment groups were designed: 5 mice receiving daily injections of saline, 5 mice receiving daily injections of Dexamethasone and 5 mice receiving daily injections of Dexamethasone plus 300 antagonist at a concentration of 6μg/g body weight. Body weight of the mice was recorded daily and monitored closely for signs of cachexia. Food and water consumption was recorded to ensure that loss in body weight was not due to a loss of appetite or thirst. Body weights, fat-pad weights, and MyoD and Pax7 expression were assessed.

Results:

Body Weight

Figure 25:
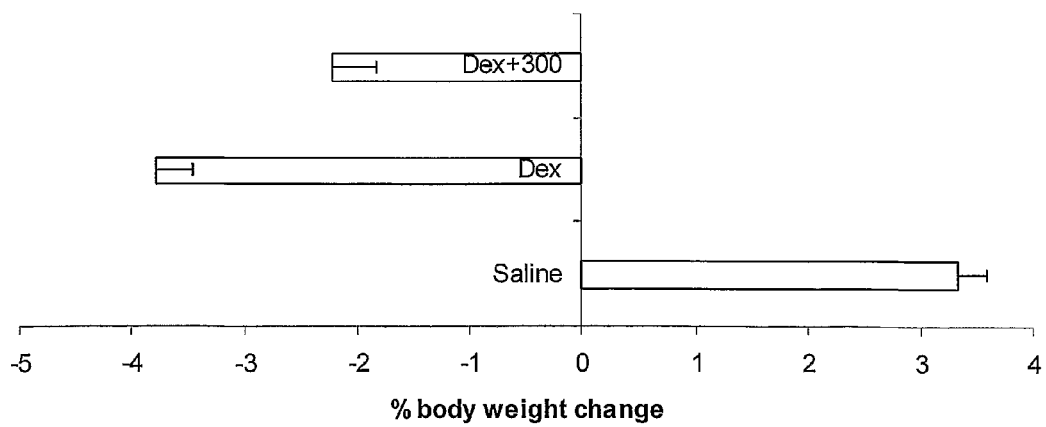
FIG. 25 shows the average % body weight change over 22 days after treatment with Dexamethasone or Dexamethasone in combination with 300.

Daily injection of Dexamethasone resulted in a reduction in average body weight as compared with saline injected controls (FIG. 25). Co-treatment with Dexamethasone and 300 antagonist resulted in a smaller average body weight loss as compared to controls (FIG. 25) indicating that the antagonists can prevent cachexia related muscle loss and hence body weight in mice. This also indicates that use of myostatin antagonists such as 300 has applications in reducing the negative effects of use of dexamethasone in human patients.

Fat Pad Weights

One of the clinical features of patients suffering from Cushing's syndrome (over-production of glucocorticoids) is increased fat deposition, therefore fat-pad weights were analysed following the completion of the trials.

Figure 26:
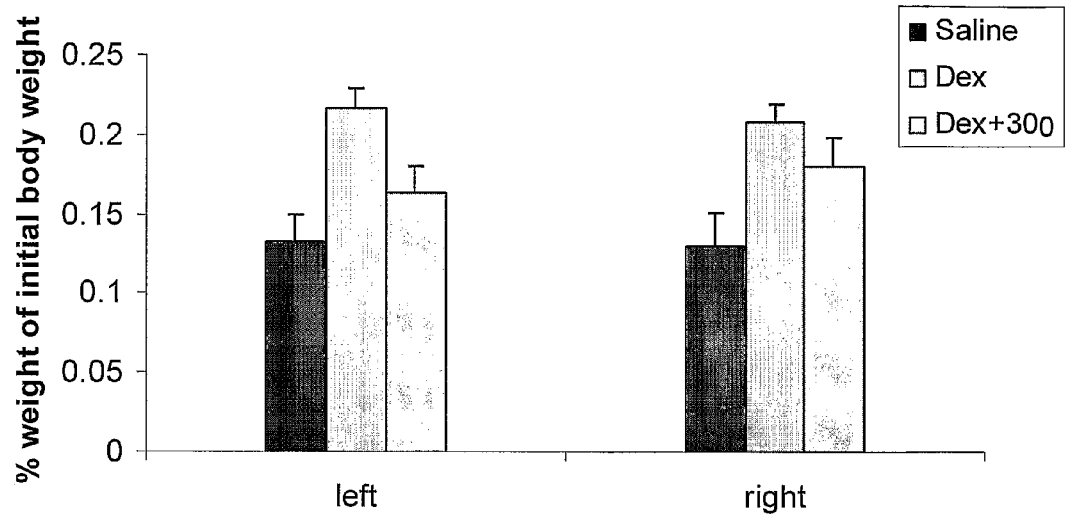
FIG. 26 shows the average retroperitoneal fat-pad weights after treatment with Dexamethasone or Dexamethasone in combination with 300.

Treatment with Dexamethasone resulted in an increase in retroperitoneal (left, 62.9%; right, 60.4%) fat-pad weights as compared to saline treated mice, with statistically significant increases observed in both the left and right retroperitoneal and inguinal fat-pads (p<0.05) (FIG. 26). An increase in retroperitoneal (left, 23.3%; right, 39.2%) and inguinal (left, 33.2%; right, 39%) fat-pad weights was also observed following treatment with 300, although to a lesser extent than that observed following treatment with Dexaniethasone only. Therefore treatment with 300 partially rescued Dexamethasone-mediated increase in fat-pad weight indicating that our antagonist can not only be useful in treating cachexia but may also be used in situation where is would be advantageous to reduce fat deposition such as in the treatment of obesity.

MyoD and Pax7 Expression

Figure 27:
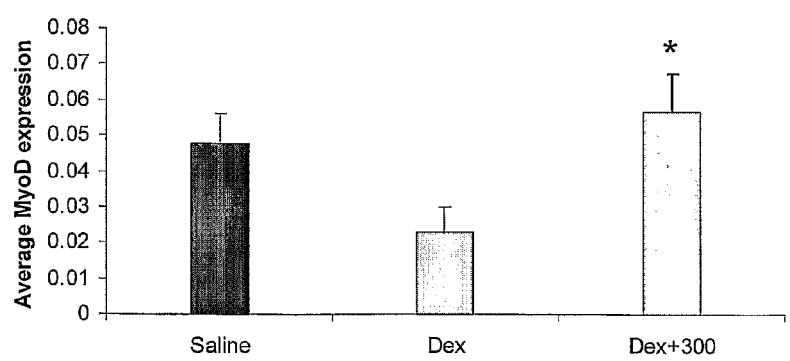
FIG. 27 shows the average MyoD expression after treatment with Dexamethasone or Dexamethasone in combination with 300.
Figure 28:
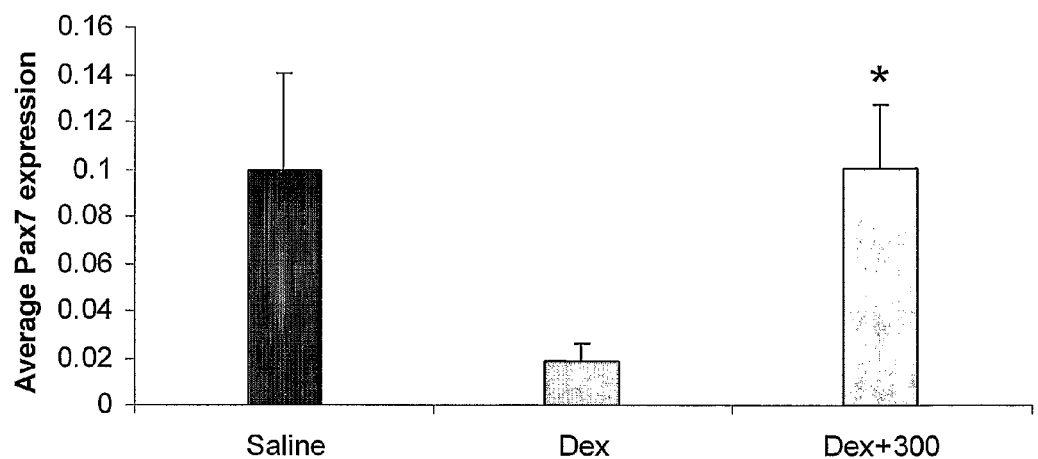
FIG. 28 shows the average Pax7 expression after treatment with Dexamethasone or Dexamethasone in combination with 300.

Protein was isolated from the right gastrocnemius muscle from all mice and Western blots performed for MyoD and Pax7. There was a significant down-regulation of MyoD (p<0.05) (FIG. 27) and Pax7 (p<0.05) (FIG. 28) expression following treatment with Dexamethasone. In addition we observed a significant up-regulation (rescue) of both MyoD (p<0.05) and Pax7 (p<0.01) in mice treated with Dexamethasone and 300 mstn antagonist. Therefore treatment with 300 antagonist appears to regulate the expression of MyoD and Pax7 during Dexamethasone-induced cachexia. It is well recognised that upregulation of MyoD and Pax 7 are markers of muscle regeneration.

During muscle regeneration in young wild-type and myostatin null mice, MyoD has been shown to be expressed earlier and at higher levels in the myostatin null muscle as compared with wild type muscle (McCroskery, 2005). Since MyoD expression can be used as a marker for the very early detection of migrating myoblasts during muscle regeneration (Grounds, 1992), this early expression of MyoD was interpreted as an advanced migration of myogenic cells to the site of injury (McCroskery, 2005).

Since Pax7 is a marker for satellite cell self-renewal (Oustanina, 2004; Zammit, 2004), the higher level of Pax7 suggests that 300 enhanced this self-renewal process. This is in accordance with an earlier finding that suggests myostatin inhibits satellite cell self-renewal (McCroskery, 2005).

Taken together, the higher Pax7 and MyoD levels resulting from the administration of 300, support the observation that 300 treatment advanced muscle regeneration in this model of muscle wasting through increasing levels of activated satellite cells and subsequent myogenesis and satellite cell self renewal.

Example 11

In Vivo Sarcopenia Trial

Methods:

Wild type mice (32 mice approx. 4-5 months of age) were injected subcutaneously fortnightly or monthly with 300 (6 μg/g body weight) or saline for a period of 10 month. Muscle strength was assessed using a grip strength apparatus (MK-380S, Muromachi; Tokyo, Japan) at the end of the trial. The maximum force exerted by a mouse while being pulled backward by the tail is recorded in Newtons. The mean of three grip tests for each mouse was calculated and the mean maximal force per group was determined.

Figure 19:
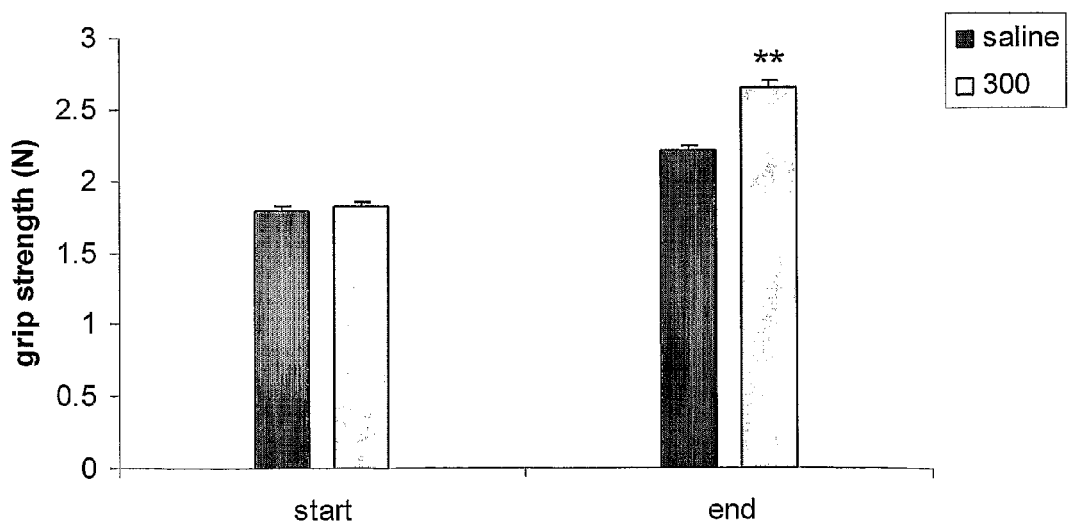
FIG. 19 shows the increase in grip strength after long term administration of 300 in wild-type mice.

Results:

Grip strength is used as an indication for muscle function (Wagner et al 2002). A 10 month animal trial was conducted to assess the effects of myostatin antagonists in improving muscle function in mice during progression from young to aged status. As shown in FIG. 19 a significant increase in grip strength in mice treated monthly with 300 over the saline control at the end of the trial indicates a functional improvement in the 300 treated mice (**p<0.01). We have shown that both application regimes, monthly (FIG. 19) as well as fortnightly (data not shown) antagonists application were equally effective in increasing muscle function most likely due to increased satellite cell activation and subsequent myogenesis.

In addition to the beneficial effects of the use of antagonists to increase muscle strength in aged mice, it was noted that during this trial the initial response after one month of treatment when the mice were young (4-5 months old) showed a significant increase in muscle strength. This shows that the antagonists are effective in increasing muscle function in muscle with normal levels of satellite cell activation and other determinants of muscle function. The result indicates that the treatment with myostatin antagonists prior to trauma due to medical treatments or prior to the onset of conditions that would be expected to result in decreased muscle strength such as enforced inactivity or other conditions.

Discussion

Myostatin is a negative regulator of muscle growth since lack of myostatin leads to muscle growth while high levels of myostatin induces muscle wasting. It is documented that myostatin elicits its biological function, in part, by controlling the proliferation rate of myoblasts (Thomas et al, 2000). Myostatin appears to be a potent regulator of cell cycle progression and it has been shown that increased levels of myostatin block the entry of myoblasts into S phase thereby inhibiting myoblast proliferation (Thomas et al, 2000). Myostatin has been shown to bind to the activin type IIB receptor and signal via the Smad2/3 pathway. It has been shown that the TGF beta members, including myostatin, contain conserved cysteine residues that are critical for determining the three dimensional structure and are essential for receptor binding (Lee and McPherron, 2001).

Inhibition of myostatin activity may manifest itself in a number of ways such as an increase in body weight (McPherron et al, 1997) enhanced muscle mass due to hypertrophy and hyperplasia (McPherron,. 1997 and Zhu et al., 2000), a reduction in body fat content (McPherron et al 2002), an increase in muscle strength (WO 2006/083183) and an increase in bone quality (Hamrick, et al 2002).

In this study, several recombinant molecules were tested for their ability to antagonise myostatin function. For the antagonists to be functional, it would be expected that the conserved cysteine residues would be critical in determining the three dimensional structure of the protein, thus imparting biological activity. Given that the C-terminal truncations at amino acid positions 300, 310, 320 and 329 all result in the loss of essential cysteine residues resulting in the disruption of the three dimensional structure, it was very surprising that 300, 310, 320 and 329 were able to be effective at neutralising myostatin activity both in vitro and in vivo. Thus these results are unprecedented and surprisingly indicate that not only are these antagonists novel compounds, but that their exact three dimensional protein structure and their mechanism of action is unpredictable. Since peptides that are C-terminally truncated at positions 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328 or 329 all contain sufficient numbers of cysteines to confer activity as demonstrated by the examples above, it is expected that all these peptides would be functional. The role of these cysteine residues in conferring function is supported by the observation that 280, which has an additional cysteine residue deleted, and therefore only contains one cysteine residue, appears to be inactive (Example 1).

The present results clearly show that the novel myostatin antagonists are able, despite the loss of key cysteine residues and associated predicted structural conformation, to antagonise myostatin. This effect has been shown in the in vitro and in vivo trials described here to provide benefits in: conditions where the effect or pathology is due to signalling via increased myostatin levels, including various wasting conditions and traumas that are associated with increased levels of myostatin, as described below, where the capacity to antagonise myostatin is likely to directly confer beneficial outcomes; and in conditions where the capacity to antagonise myostatin results in the enhancement of physiological processes such as myoblast proliferation, satellite cell activation and self-renewal, migration of myoblasts and macrophages and others, and where the enhancement of these effects confers benefits in tissues where myostatin levels are not increased above those occurring in healthy tissues.

The present invention is likely to be useful in the treatment or prevention of a number of diseases and disorders that are characterised, at least in part, by an abnormal amount, development or metabolic activity of muscle or adipose tissue in a mammal and may include disorders related to muscle hypertrophy; muscle atrophy and muscle wasting associated with inflammatory myopathies, muscular dystrophies, motor neuron diseases, diseases of the neuromuscular junction, diseases of the peripheral nerve, myopathies due to endocrine abnormalities, metabolic syndrome, HIV, cancer, sarcopenia, cachexia and other wasting conditions; cardiac failure; osteoporosis; renal failure or disease; liver failure or disease; anorexia; obesity; diabetes; and wound healing. For example, it has been shown that cachexia can be induced in mice by the systematic administration of myostatin (Zimmers et al, 2002). Myostatin levels have also been shown to be elevated in animals with burn injuries (Charles H. Lang, Christine Silvis, Gerald Nystrom And Robert A. Frost Regulation of myostatin by glucocorticoids after thermal injury, FASEB 15 1807-1809 2001) and in HIV patients (Gonzalez-Cadavid et al, 1998) and plasma myostatin immunoreactive protein was found to be increased after prolonged bedrest (Zachwieja et al. 1999). We have demonstrated that 5 administration of the antagonists of the s results in rescuing myostatin mediated cachexia signalling molecules (Example 9) and alleviating body weight loss and enhancing muscle regeneration in a cachexia mouse model (Example 10). Thus indicating that our antagonists can be useful for the treatment of individuals suffering from cachexia resulting from burns injuries, prolonged bed rest, HIV or cancer.

Treatment of conditions such as these where increased myostatin levels is believed to be a key signal to induce the deleterious effects will obviously be assisted by the capacity to antagonise the myostatin signal using antagonists such as are described here. It is understood that there will be numerous pathological conditions where the role of myostatin in signalling and induction of the pathology exists but has not been discovered as yet.

Use of the present myostatin antagonists has been shown to confer benefits in several conditions where it is not clear whether increased levels of myostatin exist or are responsible for the decline in muscle or other tissue function. It is clear that the inhibition of myostatin can confer benefits in increasing myoblast proliferation in wild type myoblasts, (Example 1), young wild type satellite cells (Example 2) and in young 5 month old mice (Example 11) where there is no indication of abnormal levels of myostatin. Data is also presented showing benefits of the present myostatin antagonists in two deleterious conditions, sarcopenia and muscular dystrophy, where the beneficial effects are likely to be largely due to the general effects of enhanced myoblast proliferation, satellite cell activation and self-renewal, migration of myoblasts and macrophages due directly to the effects of the present antagonists.

Sarcopenia or age-related cachexia is characterized by insufficient levels of muscle regeneration and reduced muscle strength due a decrease in satellite cell activity and myogenesis (Conboy et al, 2005; Bockhold et al, 1998).

It has been demonstrated that using the antagonists of the invention, muscle regeneration is increased by two main mechanisms, i.e. by increasing myoblast proliferation (Example 1), and by increasing satellite cell activation (Example 2). The increase in muscle regeneration is associated with an increase in muscle strength as shown using both short term (Example 4) and long term (Example 11) administration of the antagonists of the invention. The results demonstrated herein also provide evidence that the antagonists of the invention can be used to improve the muscle mass and strength in a number of conditions, such as muscular dystrophy (Example 5); muscle injury (Example 8); sarcopenia (Example 11); and cancer cachexia (Examples 9 and 104).

As the mechanism of action is similar for other conditions, it is predicted that antagonists will be useful for the treatment of individuals suffering from cachexia resulting from burns injuries, prolonged bed rest, HIV or cancer and sarcopenia. Further, increasing satellite cell activation and muscle strength in young wild-type muscle (Examples 2 and 11) also indicates that the antagonists will be useful for treatment of patients pre-operatively thus preventing muscle loss due to post-surgery enforced bed rest.

In dystrophic conditions there is constant activation of satellite cells due to repeated cycles of muscle degeneration and subsequent regeneration. The present results demonstrate that the inventive antagonists are able to increase muscle regeneration, satellite cell activation and muscle strength in a muscular dystrophy mouse model (Example 5). As this mouse model is a standard model for human dystrophy, it is predicted that individuals suffering from dystrophy will be able to be successfully treated with the myostatin antagonists of the present invention.

The two examples above show the effects of treatment of the antagonists on grip strength in young and old mice (Example 4) and in decreasing the symptoms in mdx mice (Example 5), where the beneficial effects are likely to be due to enhanced myoblast proliferation, satellite cell activation and self-renewal, migration of myoblasts and macrophages due to the effects of our antagonists in reducing myostatin levels below normal wild type. In addition to these examples it is expected that treatment with the present myostatin antagonists will confer beneficial effects in treatment of any medical condition where muscle function will be improved by the effects of enhanced myoblast proliferation, satellite cell activation and self-renewal, migration of myoblasts and macrophages. Such conditions include muscle loss after surgery, growth retardation, physiological short stature, muscle loss due to chronic illness, accelerating the recovery of burns patients or other disorders where improving muscle function would be beneficial.

Skeletal muscle resistance to insulin-stimulated glucose uptake is the earliest known manifestation of type 2 diabetes mellitus (Corregan et al. 1991). It has been shown that the lack of myostatin partially attenuates the obese and diabetes phenotypes of two mouse models, the agouti lethal yellow (Yen et al. 1994), and obese. Additionally the introduction of a myostatin mutation into agouti lethal yellow mice has been shown to suppress fat accumulation by five-fold (McPherron et al, 2002). This, together with the present results 5 showing that the antagonists of the present invention are capable of decreasing fat deposition (Example 4 and 11), indicate that individuals suffering from the effects of diabetes, obesity, and hyperglycemic conditions will be able to be successfully treated with a therapeutically effective dose of one or more myostatin antagonist of the present invention.

The present results also show that the present myostatin antagonists are useful in wound healing. Every wound undergoes three distinct phases of wound healing. Firstly the inflammatory phase for the detachment of deteriorated tissue and for wound cleansing; secondly a proliferative phase for the development of granulation tissue; and thirdly a differentiation or regeneration phase for maturation and scar formation (Sedlarik 1994). The inflammatory phase is characterized by infilatration of inflammatory cells such as macrophages to the damaged site. The present results demonstrate that use of the present antagonists increase the migratory capacity of macrophages (Example 3). This along with decreased wound size in skin (Example 6), decreased collagen deposition in skin (Example 7) and increased muscle regeneration as indicated by increased myogenic markers (Example 8) suggests that the present antagonists will be useful in the treatment of wound healing. The results show that the beneficial effects can be expected in wounds of various tissues where increased macrophage and myoblast migration, accelerated regeneration of muscle tissues and decreased fibrosis are useful outcomes.

It is also expected that the present myostatin antagonists will be useful in the treatment of damaged cardiac muscle. Myostatin levels are upregulated in cardiomyocytes following myocardial infarction (Sharma et al, 1999) indicating that inhibition of myostatin may improve recovery of heart muscle after infarct.

In addition, myostatin null mice have increased bone mineral content and density as well as increased muscle mass (Hamrick et al, 2002). It is therefore expected that reducing myostatin levels will improve bone strength and reduce osteoporosis and other degenerative bone diseases.

Rhabdomyosarcomas (RMSs), one of the most common solid tumor of childhood, express high levels of myostatin. It has been demonstrated that inhibition of myostatin allows RMSs to progress into the myogenic terminal differentiation (Ricaud et al, 2003), therefore our antagonists may be useful for treatment of cancer.

As discussed above, it is expected that the antagonists of the present invention will be useful for treating humans. The present antagonists will also be useful for treating other species given that the myostatin sequence is highly homologous across species, indeed the human and bovine sequences are identical (FIG. 31) and our antagonists have been demonstrated to increase proliferation of ovine, murine and human cells in vitro. The present results also clearly demonstrate that myostatin antagonists of the invention can increase proliferation of myoblasts (Example 1).

REFERENCES

The following references, to the extent that they provide exemplary, procedural or other details supplementary to those set forth herein, are specifically incorporated herein by reference. The patent specifications, referred to throughout the text of this specification, are also specifically incorporated herein by reference.

Allen, R E, Temm-Grove, C J, Sheehan, S M, and Rice, G. (1997). Skeletal muscle satellite cell cultures. Methods Cel Biol 52, 155-76.

Bemkop-Schnurch A and Walker G (2001) Multifimctional matrices for oral peptide delivery. Crit Rev Ther Drug Carrier Syst 18(5): 459-501

Berry C, Thomas M, Langley B, Sharma, M and Kambadur R (2000). Single cysteine to tyrosine transition inactivates the growth inhibitory fimction in Piedmontese myostatin. Am J Physiol Cel Physiol 283, C135-C141.

Bischoff, R. (1994). Myology, vol. 1 (eds AG. Engel and C. Franzini-Armstrong), pp. 97-118: McGraw-Hill Professional Bockliold, K. J., Rosenblatt, J. D. and Partridge, T. A. (1998). Aging normal and dystrophic mouse muscle: analysis of myogenicity in cultures of living single fibers. *Muscle Nerve* 21, 173-83

Bogdanovich S, Krag T O, Barton E R, Morris L D, Whittemore L A, Ahima R S, Khurana T S. (2002) Functional improvement of dystrophic muscle by myostatin blockade. Nature 420: 418-21

Bradley, P., Misura, K. M. S. and Baker, D. (2005) Toward High-Resolution de Novo Structure Prediction for Small Proteins. Science 309, 1868-1871

Carlson, C J, Booth, F W and Gordon, S E. (1999). Skeletal muscle myostatin mRNA expression is fibre-type specific and increases during hind-limb unloading. Am J Physiol 277, R601-6

Colditz, I G and Movat H Z (1984). Kinetics of neutrophil accumulation in acute inflammatory lesions induced by chemotaxis and chemotaxinigens. J Immunol 133, 2167-73.

Conboy, I. M., Conboy, M. J., Wagers, A. J., Girma, E. R., Weissman, I. L. and Rando, T. A. (2005). Rejuvenation of aged progenitor cells by exposure to a young systemic environment. Nature 433, 760-4;

Corrigan A Z, Bilezikjian L M, Carroll R S, Bald L N, Schmelzer C H, Fendly B M, Mason A J, Chin W W, Schwall R H, and Vale W (1991) Evidence for an autocrine role of activin B within rat anterior pituitary cultures. Endocrin 128: 1682-1684

Evan G I, Lewis G K, Ramsey G and Bishop J M (1985). Isolation of monoclonal antibodies specific for human c-myc proto-oncogene product. Mol Cel Biol 5, 3610-16.

Field J, Nikawa D, Broek B, MacDonald B, Rodgers L, Wilson I A, Lerner R A and Wigler M (1988). Purification of a RAS-responsive adenylyl cyclase complex from *Saccharomyces cerevisiae* by use of an epitope addition method. Mol Cel Biol 8, 2159-65.

Giridharan N V (1998). Animal models of obesity and their usefulness in molecular approach to obesity. Indian J Med Res 108, 225-42.

Gonzalez-Cadavid N F, Taylor W E, Yarasheski K, Sinha-Hikim I, Ma K, Ezzat S, Shen R, Lalani R, Asa S, Mamita M, Nair G, Arver S, Bhasin S. (1998) Organization of the human myostatin gene and expression in healthy men and HIV-infected men with muscle wasting. Proc Natl Acad Sci USA 95: 14938-43.

Gribskov, M., and Burgess, R. R. (1986). Sigma factors from *E. coli, B. subtilis*, phage SPO1, and phage T4 are homologous proteins.", *Nucleic Acids Research* 14, 6745-6763.

Grobet L, Martin L J, Poncelet D, et al. (1997) A deletion in the bovine myostatin gene causes the double-muscled phenotype in cattle. Nat Genet 17:71-74.

Hamrick M W, McPherron A C, Lovejoy C O. (2002) Bone mineral content and density in the humerus of adult myostatin-deficient mice. Calcif Tissue Int 71(1):63-8.

Hamrick M W (2003) Increased bone mineral density in the femora of GDF8 knockout mice. Anat Rec 272A(l): 388-91.

Hill J J, Davies M V, Pearson A A, et al. (2002) The myostatin propeptide and the follistatin-related gene are inhibitory binding proteins of myostatin in normal serum. J Biol Chem 277: 40735-40741.

Hill J J, Qiu Y, Hewick R M. (2003) Regulation of myostatin in vivo by growth and differentiation factor-associated serum protein-1: a novel protein with protease inhibitor and follistatin domains. Mol Endocrinol 17: 1144-1154.

Hopp, P., Prickett, K S, Price, V L, Libby, R T, Ceretti, D P, March, C J, Urdal, D L. and Conlon, P. J. 1988. A short polypeptide marker sequence useful for recombinant protein identification and purification. Bio/Technology 8: 1204-1210.

Jeanplong F, Sharma M, Somers W G, Bass J J and Kambadur R (2001) Genomic organization and neonatal expression of the bovine myostatin gene. Mol Cell Biochem 220: 31-37.

Jones, G E. (2000). Cellular signaling in macrophage migration and chemotaxis. J Leukoc Biol 68, 593-602.

Kambadur R., Sharma M., Smith T. and Bass J. J. (1997) Mutations in myostatin (GDF-8) in double muscled Belgian Blue and Piedmontese Cattle. Genome Res 7: 910-916.

Kirk S, Oldham J, Kambadur R, Sharma M, Dobbie P, and Bass J. (2000). Myostatin regulation during skeletal muscle regeneration. J Cel Physiol 184(3), 356-63.

Langley B, Thomas M, McFarlane C, Gilmour S, Sharma M, Kambadur R. (2004) Myostatin inhibits rhabdomyosarcoma cell proliferation through an Rb-independent pathway. Oncogene 23: 524-34.

Lee S J, McPherron A C. (2001) Regulation of myostatin activity and muscle growth. Proc Natl Acad Sci USA 98: 9306-9311.

Like A A, Rossini A A (1976). Streptozotocin-induced pancreatic insulitis: new model of diabetes mellitus. Science 193, 415-7.

Lutz-Freyernuth C, Query C C and Keene J D (1990). Quantitative Determination that One of Two Potential RNA-Binding Domains of the A Protein Component of the U1 Small Nuclear Ribonucleoprotein Complex Binds with lHigh Affinity to Stem-Loop II of U1 RNA Proc Natl Acad Sci USA 87, 6393-97.

Ma K, Mallidis C, Bhasin S, Mahabadi V, Artaza J, Gonzalez-Cadavid N, Arias J, Salehian B. (2003) Glucocorticoid-induced skeletal muscle atrophy is associated with upregulation of myostatin gene expression. Am J Physiol Endocrinol Metab 285: E363-E371.

Martin G A, Yatani R, Clark R, Conroy L, Polakis P, Brown A M and McCormick F (1992). GAP domains responsible for ras p21-dependent inhibition of muscarinic atrial K+ channel currents. Science 255, 192-4.

McCroskery S, Thomas M, Maxwell L, Sharma M, and Kambadur R. (2003). Myostatin negatively regulates satellite cell activation and self-renewal. J Cel Biol 162.

McPherron A C, Lawler A M, Lee S J. (1997a) Regulation of skeletal muscle mass in mice by a new TGF-beta superfamily member. Nature 387: 83-90.

McPherron A C, Lee S J. (1997b) Double muscling in cattle due to mutations in the myostatin gene. Proc Natl Acad Sci USA 94:12457-12461.

McPherron A C, Lee S J (2002) Suppression of body fat accumulation in myostatin-deficient mice. J Clin Invest 109: 595-601.

Needleman S B and Wunsch C D (1970). A General method applicable to the search for similarities in the amin acid sequence of two proteins. J Mol Biol 48(3), 443-53.

Nicholas G, Thomas M, Langley B, et al. (2002) Titin-cap associates with, and regulates secretion of, myostatin. J Cell Physiol 193: 120-131.

Paborsky L R, Fendly B M, Fisher K L, Lawn R M, Marks B J, McCray G, Tate, K M, Vehar G A and Gorman C M (1990). Mammalian cell transient expression of tissue factor for the production of antigen. Protein Engineering 3(6), 547-53.

Partridge T A. (1997). Tissue culture of skeletal muscle. Methods Mol Biol 75, 131-44.

Pearson W R and Lipman D J (1988). Improved tools for biological sequence comparison. Proc Natl Acad Sci USA 85(8), 2444-8.

Rebbapragada A, Benchabane H, Wrana J L, Celeste A J, Attisano L. (2003) Myostatin signals through a transforming growth factor beta-like signaling pathway to block adipogenesis. Mol Cell Biol 23: 7230-42.

Ricaud S, Vemus B, Duclos M, Bernardi H, Ritvos O, Carnac G, Bonnieu A. (2003) Inhibition of autocrine secretion of myostatin enhances terminal differentiation in human rhabdomyosarcoma cells. Oncogene. 22(51):8221-32

Rios R, Carneiro I, Arce V M, Devesa J. (2001) Myostatin regulates cell survival during $C_2C_{12}$ myogenesis. Biochem Biophys Res Commun 280: 561-566.

Rosenblatt, J. D., Lunt, A. I., Parry, D. J. and Partridge, T. A. (1995). Culturing satellite cells from living single muscle fiber explants. In Vitro Cel Dev Biol Anim 31, 773-9.

Sharma M, Kambadur R. Matthews K G, Somers W G, Devlin G P, Conaglen J V, Fowke P J, Bass J J. (1999) Myostatin, a transforming growth factor-beta superfamily member, is expressed in heart muscle and is upregulated in cardiomyocytes after infarct. J Cell Physiol 180:1-9.

Schuelke M, Wagner K R, Stolz L E, Hubner C, Riebel T, Komen W, Braun T, Tobin J F, Lee S J. (2004) Myostatin mutation associated with gross muscle hypertrophy in a child. N Engl J Med. 350(26):2682-8.

Sedlarik K. M; The Process of Wound Healing. Wung Forum. Published on-line: hartmann_online, 1994

Skinner R H, Bradley S, Brown A L, Johnson N J, Rhodes, S Stammers D K, and Lowe P N (1991) Use of the Glu-Glu-Phe C-terminal epitope for rapid purification of the catalytic domain of normal and mutant ras GTPase-activating proteins J. Biol. Chem. 266:14163 -14166

Spiller M P, Kambadur R, Jeanplong F, Thomas M, Martyn J K, Bass J J, Sharma M. (2002) The myostatin gene is a downstream target gene of basic helix-loop-helix transcription factor MyoD. Mol Cell Biol 22: 7066-82.

Tanabe Y, Esaki K, Nomura T (1986). Skeletal muscle pathology in X chromosome-linked muscular dystrophy (mdx) mouse. ActaNeuropathol (Berl) 69(1-2), 91-5.

Taylor W E, Bashin S, Artaza J, et al. (2001) Myostatin inhibits cell proliferation and protein synthesis in $C_2C_{12}$ muscle cells. Am J Physiol Endocrinol Metab 280: E221 -E228.

Thomas M, Langley B, Berry C, et al. (2000) Myostatin, a negative regulator of muscle growth, functions by inhibiting myoblast proliferation. J Biol Chem 275: 40235-40243.

Wang H, Zhang Q, Zhu D. (2003) hSGT interacts with tha N-terminal region of myostatin. Biochem Biophys Res Commun 311:877-883.

Wehling M, Cai B, and Tidball J G (2000). Modulation of myostatin expression during modified muscle use. Faseb J 14, 103-10.

Werle M. and Bernkop-Schnurch A. (2006) Strategies to improve plasma half life of peptide and protein drugs. Amino Acids 30: 351-367.

Yang L, Scott P G, Dodd C, Medina A, Jiao H, Shankowsky H A, Ghahry A and Tredget E E. (2005). Identification of fibrocytes in postburn hypertrophic scar. Wound Repair and Regeneration 13(4), 398-404.

Yen T T, Gill A M, Frigeri L G, Barsh G S and Wolff G L (1994) Obesity, diabetes, and neoplasia in yellow Avy/-mice: ectopic expression of the agouti gene, FASEB J. 8:479-488.

Zachwieja J J, Smith S R, Sinha-Hikim I, Gonzalez-Cadavid N, Bhasin S (1999) Plasma myostatin-immunoreactive protein is increased after prolonged bed rest with low-dose T3 administration. J Gravit Physiol 6: 11-5.

Zhu X, Hadhazy M, Wehling M, Tidbal J Gl, McNally E M, (2000) Dominant negative myostatin produces hypertrophy without hyperplasia in muscle. FEBS Letters 474(1): 71-75

Zimmers T A, Davies M V, Koniaris L G, Haynes P, Esquela A F, Tomlinson K N, McPherron A C, Wolfman N M, Lee S J. (2002) Induction of cachexia in mice by systemically administered myostatin. Science 296:1486-s8.

INDUSTRIAL APPLICATION

The present invention provides novel proteins having myostatin antagonistic activity which are useful in the treatment of myostatin related disorders. Such disorders are characterised, at least in part, by an abnormal amount, development or metabolic activity of muscle or adipose tissue in a mammal and may include disorders related to muscle hypertrophy; muscle atrophy and muscle wasting associated with inflammatory myopathies, muscular dystrophies, motor neuron diseases, diseases of the neuromuscular junction, diseases of the peripheral nerve, myopathies due to endocrine abnormalities, metabolic syndrome, HIV, cancer, sarcopenia, cachexia and other wasting conditions; cardiac failure; osteoporosis; renal failure or disease; liver failure or disease; anorexia; obesity; diabetes; and wound healing.

What we claim is:

1. An isolated recombinant polypeptide consisting of the amino acid sequence of SEQ ID NO: 6 or an amino acid sequence that has at least 95% sequence identity to SEQ ID NO: 6.

2. An isolated recombinant polypeptide of claim 1 wherein the amino acid sequence comprises one or more modified amino acid residues selected from the group consisting of a glycosylated amino acid, a PEGylated amino acid, a farnesylated amino acid, an acetylated amino acid, a biotinylated amino acid, an amino acid conjugated to a lipid moiety and a D amino acid.

3. A method to treat or reduce the severity of a pathologic condition, wherein the pathologic condition is selected from the group consisting of muscular dystrophies, sarcopenia, cachexia and obesity, wherein said method comprises administering an effective amount of at least one polypeptide of claim 1 to a patient in need thereof.

4. A method to increase satellite cell activation, myoblast proliferation, macrophage and myoblast migration and/or to reduce fibrosis after wound healing in a subject comprising administering an effective amount of at least one polypeptide of claim 1 to a patient in need thereof.

5. A method as claimed in claim 4, whereby administration is daily.

6. A method as claimed in claim 4, whereby administration is three times a week.

7. A method as claimed in claim 4, whereby administration is once a fortnight.

8. A method as claimed in claim 4, whereby administration is once a month.

9. A pharmaceutical composition comprising the isolated polypeptide of claim 1 together with a pharmaceutically acceptable carrier.

10. A pharmaceutical composition as claimed in claim 9, wherein the isolated polypeptide is conjugated to a second pharmaceutically active compound having muscle growth-promoting activity to enhance myostatin receptor antagonist activity in a target cell or tissue, and wherein the pharmaceutical composition is formulated for separate, sequential or simultaneous administration of the isolated polypeptide and the second compound.

11. A method of improving muscle strength or reducing fat deposition in an animal comprising administering to said animal an effective amount of at least one polypeptide of claim 1 to the animal.

12. A method as claimed in claim 11, wherein the animal is selected from the group consisting of sheep, cattle, deer, poultry, turkey, pig, horse, mouse, rat, cat, dog and human.

13. A method to treat or reduce the severity of sarcopenia, wherein an effective amount of at least one polypeptide of claim 1 is administered to a patient in need thereof.

* * * * *

SEQUENCE LISTING

```
<160> NUMBER OF SEQ ID NOS: 14

<210> SEQ ID NO 1
<211> LENGTH: 2823
<212> TYPE: DNA
<213> ORGANISM: Homo sapiens

<400> SEQUENCE: 1
agattcactg gtgtggcaag ttgtctctca gactgtacat gcattaaaat tttgcttggc      60
attactcaaa agcaaaagaa aagtaaaagg aagaaacaag aacaagaaaa aagattatat     120
tgattttaaa atcatgcaaa aactgcaact ctgtgtttat atttacctgt ttatgctgat     180
tgttgctggt ccagtggatc taaatgagaa cagtgagcaa aaagaaaatg tggaaaaaga     240
ggggctgtgt aatgcatgta cttggagaca aaacactaaa tcttcaagaa tagaagccat     300
taagatacaa atcctcagta aacttcgtct ggaaacagct cctaacatca gcaaagatgt     360
tataagacaa cttttaccca aagctcctcc actccgggaa ctgattgatc agtatgatgt     420
ccagagggat gacagcagcg atggctcttt ggaagatgac gattatcacg ctacaacgga     480
```

```
aacaatcatt accatgccta cagagtctga ttttctaatg caagtggatg gaaaacccaa      540
atgttgcttc tttaaattta gctctaaaat acaatacaat aaagtagtaa aggcccaact      600
atggatatat ttgagacccg tcgagactcc tacaacagtg tttgtgcaaa tcctgagact      660
catcaaacct atgaaagacg gtacaaggta tactggaatc cgatctctga aacttgacat      720
gaacccaggc actggtattt ggcagagcat tgatgtgaag acagtgttgc aaaattggct      780
caaacaacct gaatccaact taggcattga aataaaagct ttagatgaga atggtcatga      840
tcttgctgta accttcccag gaccaggaga agatgggctg aatccgtttt tagaggtcaa      900
ggtaacagac acaccaaaaa gatccagaag ggattttggt cttgactgtg atgagcactc      960
aacagaatca cgatgctgtc gttaccctct aactgtggat tttgaagctt tggatgggga     1020
ttggattatc gctcctaaaa gatataaggc caattactgc tctggagagt gtgaatttgt     1080 attttttacaa aaatatcctc atactcatct ggtacaccaa gcaaacccca gaggttcagc     1140
aggcccttgc tgtactccca caaagatgtc tccaattaat atgctatatt ttaatggcaa     1200
agaacaaata atatatggga aaattccagc gatggtagta gaccgctgtg ggtgctcatg     1260
agatttatat taagcgttca taacttccta aaacatggaa ggttttcccc tcaacaattt     1320
tgaagctgtg aaattaagta ccacaggcta taggcctaga gtatgctaca gtcacttaag     1380
cataagctac agtatgtaaa ctaaaagggg aatatatgc aatggttggc atttaaccat      1440
ccaaacaaat catacaagaa agttttatga tttccagagt ttttgagcta aaggagatc      1500 aaattacatt tatgttccta tatattacaa catcggcgag gaaatgaaag cgattctcct     1560
tgagttctga tgaattaaag gagtatgctt taaagtctat ttctttaaag ttttgtttaa     1620
tatttacaga aaaatccaca tacagtattg gtaaaatgca ggattgttat ataccatcat     1680
tcgaatcatc cttaaacact tgaatttata ttgtatggta gtatacttgg taagataaaa     1740
ttccacaaaa atagggatgg tgcagcatat gcaatttcca ttcctattat aattgacaca     1800
gtacattaac aatccatgcc aacggtgcta atacgatagg ctgaatgtct gaggctacca     1860
ggtttatcac ataaaaaaca ttcagtaaaa tagtaagttt ctctttttctt caggggcatt     1920 ttcctacacc tccaaatgag gaatggattt tctttaatgt aagaagaatc attttttctag    1980 aggttggctt tcaattctgt agcatacttg gagaaactgc attatcttaa aaggcagtca     2040
aatggtgttt gttttatca aaatgtcaaa ataacatact tggagaagta tgtaattttg      2100
tctttggaaa attcaacac tgcctttgca acactgcagt ttttatggta aaataataga      2160
aatgatcgac tctatcaata ttgtataaaa agactgaaac aatgcattta tataatatgt     2220
atacaatatt gttttgtaaa taagtgtctc cttttttatt tactttggta tattttttaca    2280 ctaaggacat ttcaaattaa gtactaaggc acaaagacat gtcatgcatc acagaaaagc     2340
aactacttat atttcagagc aaattagcag attaaatagt ggtcttaaaa ctccatatgt     2400
taatgattag atggttatat tacaatcatt ttatattttt ttacatgatt aacattcact     2460
tatggattca tgatggctgt ataaagtgaa tttgaaattt caatggttta ctgtcattgt     2520
gtttaaatct caacgttcca ttattttaat acttgcaaaa acattactaa gtataccaaa     2580
ataattgact ctattatctg aaatgaagaa taaactgatg ctatctcaac aataactgtt     2640
acttttattt tataatttga taatgaatat ttttctgcat ttatttactt ctgttttgta     2700
aattgggatt ttgttaatca aatttattgt actatgacta aatgaaatta tttcttacat     2760
ctaatttgta gaaacagtat aagttatatt aaagtgtttt cacattttttt tgaaagacaa     2820 aaa                                                                    2823
```

```
<210> SEQ ID NO 2
<211> LENGTH: 375
<212> TYPE: PRT
<213> ORGANISM: Homo sapiens

<400> SEQUENCE: 2

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365

Val Asp Arg Cys Gly Cys Ser
    370                 375
```

<210> SEQ ID NO 3
<211> LENGTH: 63
<212> TYPE: PRT
<213> ORGANISM: Homo sapiens

<400> SEQUENCE: 3

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln
    50                  55                  60

<210> SEQ ID NO 4
<211> LENGTH: 54
<212> TYPE: PRT
<213> ORGANISM: Homo sapiens

<400> SEQUENCE: 4

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys
    50

<210> SEQ ID NO 5
<211> LENGTH: 44
<212> TYPE: PRT
<213> ORGANISM: Homo sapiens

<400> SEQUENCE: 5

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser
        35                  40

<210> SEQ ID NO 6
<211> LENGTH: 34
<212> TYPE: PRT
<213> ORGANISM: Homo sapiens

<400> SEQUENCE: 6

Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala

<210> SEQ ID NO 7
<211> LENGTH: 28
<212> TYPE: PRT
<213> ORGANISM: Homo sapiens

<400> SEQUENCE: 7

```
Phe Gly Leu Asp Cys Asp Glu His Ser Thr Glu Ser Arg Cys Cys Arg
1               5                   10                  15

Tyr Pro Leu Thr Val Asp Phe Glu Ala Phe Gly Trp
            20                  25

<210> SEQ ID NO 8
<211> LENGTH: 23
<212> TYPE: PRT
<213> ORGANISM: Homo sapiens

<400> SEQUENCE: 8

Asp Phe Gly Leu Asp Cys Asp Glu His Ser Thr Glu Ser Arg Cys Cys
1               5                   10                  15

Arg Tyr Pro Leu Thr Val Asp
            20

<210> SEQ ID NO 9
<211> LENGTH: 18
<212> TYPE: PRT
<213> ORGANISM: Homo sapiens

<400> SEQUENCE: 9

Asp Phe Gly Leu Asp Cys Asp Glu His Ser Thr Glu Ser Arg Cys Cys
1               5                   10                  15

Arg Tyr

<210> SEQ ID NO 10
<211> LENGTH: 16
<212> TYPE: PRT
<213> ORGANISM: Homo sapiens

<400> SEQUENCE: 10

Asp Phe Gly Leu Asp Cys Asp Glu His Ser Thr Glu Ser Arg Cys Cys
1               5                   10                  15

<210> SEQ ID NO 11
<211> LENGTH: 15
<212> TYPE: PRT
<213> ORGANISM: Homo sapiens

<400> SEQUENCE: 11

Asp Phe Gly Leu Asp Cys Asp Glu His Ser Thr Glu Ser Arg Cys
1               5                   10                  15

<210> SEQ ID NO 12
<211> LENGTH: 14
<212> TYPE: PRT
<213> ORGANISM: Homo sapiens

<400> SEQUENCE: 12

Asp Phe Gly Leu Asp Cys Asp Glu His Ser Thr Glu Ser Arg
1               5                   10

<210> SEQ ID NO 13
<211> LENGTH: 26
<212> TYPE: PRT
<213> ORGANISM: Artificial Sequence
<220> FEATURE:
<223> OTHER INFORMATION: Synthetic peptide

<400> SEQUENCE: 13

Met Gly His His His His His His His His His Ser Ser Gly His
1               5                   10                  15
```

```
Ile Glu Gly Arg His Met Leu Glu Asp Pro
            20                  25

<210> SEQ ID NO 14
<211> LENGTH: 21
<212> TYPE: PRT
<213> ORGANISM: E. coli

<400> SEQUENCE: 14

Glu Asp Pro Ala Ala Asn Lys Ala Arg Lys Glu Ala Glu Leu Ala Ala
1               5                   10                  15

Ala Thr Ala Glu Gln
            20
```